United States Patent [19]

Nishimura et al.

[11] 4,171,340
[45] Oct. 16, 1979

[54] FUMIGATING APPARATUS AND METHOD

[75] Inventors: Akira Nishimura; Takanobu Kashihara; Fukuyasu Okuda; Masanaga Yamaguchi, all of Ako, Japan

[73] Assignee: Earth Chemical Company, Ltd., Hyogo, Japan

[21] Appl. No.: 882,816

[22] Filed: Mar. 2, 1978

[30] Foreign Application Priority Data

| Mar. 3, 1977 | [JP] | Japan | 52-23475[U] |
| Mar. 18, 1977 | [JP] | Japan | 52-33445[U] |
| Mar. 18, 1977 | [JP] | Japan | 52-33446[U] |
| Apr. 27, 1977 | [JP] | Japan | 52-54648[U] |
| May 13, 1977 | [JP] | Japan | 52-61975[U] |
| Jun. 6, 1977 | [JP] | Japan | 52-74167[U] |
| Jul. 23, 1977 | [JP] | Japan | 52-98584[U] |

[51] Int. Cl.² .......... A61L 1/00; A61L 3/00; A01M 13/00
[52] U.S. Cl. .......... 422/36; 43/125; 43/129; 71/DIG. 1; 252/350; 422/1; 422/28; 422/37; 422/305; 424/40
[58] Field of Search .......... 21/117, 119, 108; 43/125, 129; 252/350; 424/40, 41, 42; 23/282; 422/28, 29, 30, 31, 32, 33, 34, 35, 36, 37, 39, 125, 305, 1; 71/DIG. 1

[56] References Cited

U.S. PATENT DOCUMENTS

| 586,759 | 7/1897 | Cock | 21/117 |
| 1,652,291 | 12/1927 | Tanner | 21/108 UX |
| 2,071,171 | 2/1937 | McConnell | 424/42 X |
| 2,440,082 | 4/1948 | Flanders et al. | 21/108 UX |
| 2,497,612 | 2/1950 | Katzman | 21/117 |
| 2,540,095 | 2/1951 | Buehler | 21/119 UX |
| 2,590,529 | 3/1952 | Gillies et al. | 21/108 UX |
| 2,682,461 | 6/1954 | Hutchison | 424/40 X |
| 2,690,501 | 9/1954 | Laibow | 21/119 X |
| 2,767,511 | 10/1956 | Kissner et al. | 21/119 X |
| 2,813,187 | 11/1957 | Rovira | 21/119 X |
| 3,446,893 | 5/1969 | Hanford et al. | 252/350 X |
| 3,645,931 | 2/1972 | Normanton et al. | 252/350 X |
| 3,806,323 | 4/1974 | Thompson | 23/282 X |
| 3,903,015 | 9/1975 | Roos et al. | 252/350 |
| 3,956,849 | 5/1976 | Radulescu | 424/42 X |
| 3,986,838 | 10/1976 | Reichert | 23/282 X |

FOREIGN PATENT DOCUMENTS

| 46-19080 | 5/1971 | Japan | 21/108 |
| 50-125039 | 10/1975 | Japan | 21/108 |
| 673429 | 6/1952 | United Kingdom | 21/119 |
| 699766 | 11/1953 | United Kingdom | 21/117 |

*Primary Examiner*—Barry S. Richman
*Attorney, Agent, or Firm*—Armstrong, Nikaido, Marmelstein & Kubovcik

[57] ABSTRACT

A mixture of an active ingredient such as insecticide, fungicide, antiseptic or the like and a blowing agent is heated indirectly with a heat evolved by contacting an exothermic substance with water to decompose the blowing agent and to volatilize the active agent. The mixture is accommodated in at least one compartment of a container while the exothermic substance is accommodated in at least one further compartment provided with water supplying means, said compartments being separated from each other by a partition which provides a heat transferring surface.

29 Claims, 47 Drawing Figures

FUMIGATING APPARATUS AND METHOD

This invention relates to a method of fumigating the interior of rooms and other confined spaces for controlling vermin and for fungicidal and incensing purposes, and an apparatus therefor, and more particularly to fumigating method and apparatus which are capable of concentrically producing such effects within a short period of time e.g. a few minutes or ten-odd minutes. The present method and apparatus are especially useful for controlling noxious insects, such as mosquitoes, flies and cockroaches, which are detrimental to man and also other insects, such as plant lice, green house whiteflies and caterpillars, which are harmful to agricultural plants.

As a method of controlling noxious insects, fumigation is known in which compositions of an active chemical and a combustible material are used, such that the combustible material, when burned, gives off heat and smoke, the heat causing the active ingredient to concentrically vaporize within a short time and the smoke assisting the volatilization of the ingredient. In order to quickly volatilize a great amount of active ingredient, the combustible materials useful for fumigating compositions are those capable of evolving a large quantity of smoke. The large quantity of smoke emitted by such combustile material generally has a pungent odor and high toxicity, is harmful to the human body and might possibly be mistaken for a fire. Soot and the like contained in the smoke tend to soil household furniture and walls in rooms. The combustible material involves a fire hazard. Fumigators must therefore be handled with care. The known fumigators further have the serious drawback that the heat of combustion of the combustible material decomposes part of the active ingredient and results in a loss of the active ingredient, consequently affording a lower volatilization efficiency, namely lower effective fugacity rate and reduced efficacy. Measurements in the above method using various insecticides indicate effective fugacity rates lower than 10%. Thus the fumigators heretofore known are not usable with safety and convenience and are unsatisfactory in effectiveness.

An object of this invention is to provide a fumigating method which can be practiced with high safety substantially free of attendant smoke and without involving combustion and an apparatus therefor.

Another object of this invention is to provide a fumigating method and an apparatus therefor capable of effectively quickly giving off the vapor of an active ingredient without entailing a loss of the active ingredient due to the thermal decomposition thereof.

Still another object of this invention is to provide a fumigating method and an apparatus therefor capable of giving off the vapor of an active ingredient uniformly throughout a confined space within a short period of time to produce greatly improved insect-controlling effects.

These and other objects of this invention will become apparent from the following description.

This invention provides a fumigating method comprising heating indirectly a mixture of an active ingredient and a blowing agent with a heat evolved from an exothermic substance which evolves heat by contact with water, decomposing the blowing agent and volatilizing the active ingredient. Further, this invention provides a fumigating apparatus comprising a container having at least one compartment accommodating a mixture of an active ingredient and a blowing agent and at least one further compartment provided adjacent thereto and accommodating an exothermic substance which evolves heat by contact with water, the interior of the container being divided with a partition into said compartments, the partition providing a surface for transferring the heat evolved from said exothermic substance to the mixture, the compartment accommodating the exothermic substance being provided with water supplying means.

We have conducted extensive research to fulfil the foregoing objects. In the course of our research, we conceived the novel idea that the heating method utilizing a chemical exothermic reaction would be more useful than the use of combustible material conventionally resorted to. Based on this concept, we prepared a mixture of an active ingredient and an exothermic substance which evolves heat on contact with water and added water directly to the mixture, thereby volatilizing the active ingredient with the heat given off by the exothermic substance. This method led to the volatilization of the active ingredient with heat, but was found to be very low in the fugacity rate of the active ingredient and infeasible. Subsequently we attempted a composition composed of the above-mentioned mixture and a blowing agent admixed therewith. However, after direct addition of water to the composition, this attempt was found to still achieve a low fugacity rate of the active ingredient. During the following research, we have found that the active ingredient can be volatilized with a greatly increased efficiency substantially free of thermal decomposition when the mixture of the active ingredient and blowing agent is heated indirectly with a heat evolved from the exothermic substance to thermally decompose the blowing agent and to volatilize the active ingredient. Thus this invention has been accomplished.

The fumigating apparatus of this invention are capable of effectively and quickly emitting a large quantity of the vapor of an active ingredient throughout a wide space without involving combustion or producing smoke which would have toxicity and pungent odor and without involving any loss of the active ingredient due to the thermal decomposition. Furthermore the apparatus of this invention, which do not require the use of any igniting means, are free of fire hazards, do not necessitate any power supply which would possibly produce an electric shock and are usable at any place desired.

The active ingredients useful in this invention are various and include those heretofore used for insecticidal, fungicidal and incensing purposes. Typical useful examples are as follows.

1. Insecticide (1) 3-allyl-2-methylcyclopenta-2-ene-4-one-1-yl dl-cis/-trans-chrysanthemate(available under the trademark "Pynamin", product of SUMITOMO CHEMICAL CO., LTD., Japan, hereinafter referred to as "allethrin A");

(2) 3-allyl-2-methylcyclopenta-2-ene-4-one-1-yl d-cis/-trans-chrysanthemate(available under the trademark "Pynamin-forte", product of SUMITOMO CHEMICAL CO., LTD., Japan, hereinafter referred to as "allethrin B");

(3) d-3-allyl-2-methylcyclopenta-2-ene-4-one-1-yl d-trans-chrysanthemate(available under the trademark "Exlin", product of SUMITOMO CHEMICAL CO., LTD., Japan);

(4) 3-allyl-2-methylcyclopenta-2-ene-4-one-1-yl d-trans-chrysanthemate;

(5) N-(3,4,5,6-tetrahydrophthalimide)-methyl dl-cis-/trans-chrysanthemate(available under the trademark "Neopynamin", product of SUMITOMO CHEMICAL CO., LTD., Japan, hereinafter referred to as "phthalthrin");

(6) 5-benzyl-3-furylmethyl d-cis/trans-chrysanthemate (available under the trademark "Chrysron-forte", product of SUMITOMO CHEMICAL CO., LTD., Japan, hereinafter referred to as "resmethrin");

(7) 5-propargyl-3-furylmethyl chrysanthemate;

(8) 3-phenoxybenzyl-2, 2-dimethyl-3-(2', 2'-dichloro)-vinylcyclopropane-carboxylate (available under the trademark "Eksmin", product of SUMITOMO CHEMICAL CO., LTD., Japan, hereinafter referred to as "permethrin");

(9) 3-phenoxybenzyl d-cis/trans-chrysanthemate (available under the trademark "Sumithrin", produce of SUMITOMO CHEMICAL CO., LTD., Japan, hereinafter referred to as "phenothrin");

(10) 0,0-dimethyl 0-(2,2-dichloro) vinylphosphate (hereinafter referred to as "DDVP");

(11) o-isopropoxyphenyl methylcarbamate;

(12) 0,0-dimethyl 0-(3-methyl-4-nitrophenyl)phosphorothioate;

(13) 0,0-diethyl 0-2-isopropyl-4-methyl-pyrimidyl-(6)-thiophosphate;

(14) 0,0-dimethyl S-(1,2-dicarboethoxyethyl)-dithiophosphate.

Among those insecticides, allethrin A, allethrin B, phthalthrin, resmethrin, permethrin, phenothrin and DDVP are most preferable.

2. Industrial fungicide (1) 2,4,4,'-trichloro-2'-hydroxydiphenyl ether (hereinafter referred to as "IF-1");

(2) 2,3,5,6-tetrachloro-4-(methylsulfonyl)-pyridine (hereinafter referred to as "IF-2");

(3) alkylbenzyl dimethylammonium chloride (to be referred to as "IF-3");

(4) benzyldimethyl {2-[2-(p-1,1,3,3-tetramethyl-butyl-phenoxy)-ethoxy]ethyl}ammonium chloride (to be referred to as "IF-4");

(5) N,N-dimethyl-N-phenyl-N'-(fluorodichloro methylthio)-sulfonamide (hereinafter referred to as "IF-5");

(6) 2-(4'-thiazolyl)benzimidazole (hereinafter referred to as "IF-6");

(7) N-(fluorodichloromethylthio)-phthalimide (hereinafter referred to as "IF-7");

(8) 6-acetoxy-2,4-dimethyl-m-dioxine (hereinafter referred to as "IF-8");

(9) salicylic acid;

(10) formalin;

(11) 4-isopropyltropolone;

(12) p-chloro-m-xylenol;

(13) zinc bis (2-pyridinethiol-1-oxide);

(14) sodium-2-pyridinethiol-1-oxide;

(15) diiodo methyl-p-tolyl-sulfone;

(16) p-chlorophenyl-diiodomethyl sulfone;

(17) 2,4-hexadienoic acid;

(18) N-(trichloromethylthio)-4-cyclohexene-1,2-dicarboximide;

(19) 2,4,5,6-tetrachloro isophthalonitrile;

(20) butyl-p-hydroxybenzoate;

(21) 3-trifluoromethyl-4,4'-dichlorocarbanilide;

(22) 2,2'-methylenebis[3,4,6-trichlorophenol];

(23) 2-hydroxyethyl-disulfide;

(24) β-phenoxyethylalcohol;

(25) 1,3-benzenediol;

(26) 1-dodecyl-2-methyl-3-benzyl-imidazolium chloride;

(27) alkyl-diaminoethylene glucine HCl;

(28) polymeric biguanide HCl;

(29) polyoctyl polyamino ethylglycine;

(30) hexahydro-1,3,5-tris-(2-hydroxyethyl)-S-triazine;

(31) polyhexamethylene biguanide HCl;

(32) poly[oxyethylene (dimethylimino) ethylene dichloride];

(33) alkylbetaine type S.A.A.;

(34) bis-(p-chlorophenyldiguanide)-hexanegluconate;

(35) S-bromo-S-nitro-1,3-dioxane;

(36) A mixture of 1,2-benzoisothiazoline-3-one, quartenary ammonium salt and propylene glycol;

(37) alkyldi (aminoethyl)glycine;

(38) alkylisoquinolinium bromide;

(39) 3,4,4'-trichlorocarbanilide;

(40) decamethylene-bis-(4-aminoquinaldinium chloride);

(41) sodium dehydroxyacetate;

(42) 1-oxy-3-methyl-4-isopropylbenzene;

(43) 2-bromo-2-nitropropane-1,3-diol;

(44) sodium p-toluenesulfon chloramide;

(45) 1-hexadecylpyridinium chloride;

(46) hexadecyltrimethylammonium bromide.

Among those industrial fungicides, IF-1 to IF-8 are preferable.

3. Antiseptic (1) α-bromo-cinnamaldehyde;

(2) N,N-dimethyl-N-phenyl-N'-(fluorodichloromethylthio)sulfamide.

4. Agricultural fungicide (1) A mixture of bis (dimethylthiocarbamoyl)disulfide, zinc dimethyldithiocarbamate and methylarsenic dimethyldithiocarbamate;

(2) S-benzyl diisopropyl phosphorothioate;

(3) O-ethyl diphenyl phosphorodithioate;

(4) diethyl 4,4'-o-phenylenebis (3-thioallophanate);

(5) dimethyl 4,4,'-o-phenylenebis (3-thioallophanate);

(6) N-(trichloromethylthio)-4-cyclohexene-1,2-dicarboximide;

(7) N-(1,1,2,2-tetrachloroethylthio)-4-cyclohexene-1,2-dicarboximide;

(8) S,S-6-methylquinoxaline-2,3-diyldithiocarbonate;

(9) pentachloronitrobenzene;

(10) methyl 1-(butylcarbamoyl)-2-benzimidazol carbamate;

(11) 2,4-dichloro-6-(o-chloroanilino)-1,3 5-triazine;

(12) 2,3-dicyano-1,4-dithia-1,4-dihydroanthraquinone;

(13) 3-hydroxy-5-methylisoxazole;

(14) streptomycin;

(15) polyoxin;

(16) blasticidin S;

(17) kasugamycin;

(18) validamycin;

(19) 4,5,6,7-tetrachlorophthalide;

(20) N-(dichlorofluoromethylthio)-N',N'-dimethyl-N-phenylsulfamide;

(21) tetrachloroisophthalonitrile;

(22) 2,4-dichloro-6-(o-chloroanilino)-1,3,5-triazine;

(23) ethyl p,p'-dichlorobenzylate;

(24) zinc ethylenebis (dithiocarbamate);

(25) manganese ethylenebis(dithiocarbamate);
(26) complex of zinc and manganese ethylenebis(dithiocarbamate);
(27) dizinc bis(dimethyldithiocarbamate)ethylene bis(dithiocarbamate);
(28) bis(dimethyl-thiocarbamoyl)disulfide;
(29) isomeric reaction mixture of 2,6-dinitro-4-octylphenyl crotonate.

Among the above fungicides, those numbered (21)–(29) are preferable.

5. Plant growth regulant (1) 4-chlorophenoxy acetic acid;
(2) gibberellin;
(3) N-(dimethylamino) succinamide;
(4) α-naphthylacetamide.

6. Herbicide (1) 2,4-D sodium salt;
(2) 3,4-dichloropropionanilide.

7. Repellent (1) 2,3,4,5-bis (Δ2-butylene)-tetrahydrofulfural;
(2) di-n-butyl-succinate.

Among the above active ingredients, insecticides are more suited for use in the apparatus of this invention. These active ingredients can be used conjointly with any of synergists, fugacity rate improving agents, deodorants, perfumes, etc. which are usually used. Preferable examples of the synergists are piperonyl butoxide, N-propyl isome, "MGK-264" (product of MCLAUGHLIN GORMLEY KING CO., U.S.A.), "Cynepirin-222" (product of YOSHITOMI PHARMACEUTICAL INDUSTRIES LTD., Japan), "Cynepirin-500" (product of YOSHITOMI PHARMACEUTICAL INDUSTRIES LTD., Japan), "Lethane 384" (product of ROHM AND HAAS COMPANY, U.S.A.), "IBTA" (product of NIPPON FINE CHEMICAL CO., LTD., Japan), "S-421" (product of SANYO CHEMICAL INDUSTRIES, LTD., Japan). Preferable fugacity rate improving agents include phenethylisothiocyanate, dimethylester of himic acid, etc. Preferred deodorants are lauryl methacrylate (LMA), etc. Citral and citronellal are preferably usable as perfumes.

The blowing agent to be used conjointly with the active ingredient and, when desired, with various additives can be any of those generally used and capable of mainly evolving nitrogen gas on thermal decomposition. It is preferable to use compounds which will give off a gas at a temperature of between about 70° C. and about 300° C. The compounds having blowing temperatures far lower than 70° C. tend to decompose by themselves during storage. The compounds with blowing temperatures much higher than 300° C. are likely not to decompose when subjected to heat evolved from the exothermic substance. Accodingly such compounds are not preferable. Examples of typical blowing agents are listed in Table 1 below.

Table 1

| No. | Blowing agent | Abbreviation | Blowing temp.(°C.) |
|---|---|---|---|
| 1. | azodicarbonamide | AC | 200–210 |
| 2. | benzenesulfonylhydrazide | BSH | 100–160 |
| 3. | p-toluenesulfonylhydrazide | TSH | 110 |
| 4. | p,p'-oxybis(benzenesulfonylhydrazide | OSH | 140–160 |
| 5. | dinitrosopentamethylene-tetramine | DPT | 190–205 |
| 6. | N,N'-dinitroso-N,N'-dimethylterephthalamide | DDTP | 90–105 |
| 7. | trihydrazinotriazine | THT | 235–290 |
| 8 | azodisisobutyranitrile | AIBN | 95–105 |
| 9. | 4,41'-azobiscyanoraleric acid | ACVA | 120 |
| 10. | t-butylazoformamide | BAFA | 147–149 |
| 11. | 2,4-bis-(azosulfonyl) toluene | 2,4-TSH | 108–109 |
| 12. | 2,2'-azobisisobutyroamide | AZ-A | 92 |
| 13. | methyl-2,2'-azobisisobutyrate | AZ-B | 85 |
| 14. | 2-(carbamoylazo)isobutyronitrile | CIB | 105 |
| 15. | 1,1'-azobiscyclohexane carbonitrile | ACHC | 115 |

Among the blowing agents listed in Table 1, AC, OSH, DPT, AIBN and ACHC are preferable because they contribute much to the increase in fugacity rate of an active ingredient. AC in particular remarkably enhances the fugacity rate thereof, substantially free of toxicity and pungent odor, and is therefore especially useful.

A blowing agent may be used with additives to reduce the blowing temperature. Preferable examples of the additives are as follows: "Dyhos" (product of NATIONAL LEAD CO., LTD., U.S.A.), "Tribase" (product of NATIONAL LEAD CO., LTD., U.S.A.), "OF-14" (product of ADECA ARGUS CO., LTD., U.S.A.), "OF-15" (product of ADECA ARGUS CO., LTD., U.S.A.), "KV-68A-1" (product of KYODO YAKUHIN CO., LTD., Japan), "Mark-553" (product of ARGUS CHEMI. CO., LTD., U.S.A.), "Sicostab 60" (product of G. Siegle & Co., U.S.A.), "Sicostab 61" (product of G. Siegle & Co., U.S.A.), Cd-stearate, Ca-stearate, Zn-stearate, Zn-octate, ZnO, Sn-maleate, $ZnCO_3$, urea, chrome yellow, carbon black, etc.

According to this invention, the amount of the blowing agent relative to the active ingredient can be determined suitably depending on the use of the resulting composition. Usually it is preferable to use at least about one part by weight of the blowing agent per part by weight of the active ingredient. The effective fugacity rate progressively increases with increasing proportion of the blowing agent, but the use of too great an amount of the blowing agent will not produce significantly improved results. Preferably about one to about 20 parts by weight of the blowing agent is used per part by weight of the active ingredient. The active ingredient and the blowing agent are merely mixed together to prepare a fumigating mixture of this invention but, to ensure efficient production and ease of use, it is desirable to prepare the mixture in the form of powders, granules, pellets, otherwise shaped pieces, paste or the like or to enclose the mixture in a bag of meltable and incombustible resin. The mixture may also be enclosed in an openable bag made of aluminum.

The exothermic substance useful in this invention for heating the mixture of active ingredient and blowing agent is any of those capable of evolving heat on contact with water so that the heat can thermally decompose the blowing agent and volatilize the active ingredient. Examples of typical exothermic substances are calcium oxide, magnesium chloride, aluminum chloride, calcium chloride and ferric chloride in the form of small pieces or grains. Among these substances, calcium oxide is most preferable since this compound gives off heat enough to elevate the temperature of the mixture of active ingredient and blowing agent up to about 400° C. without producing any harmful substance due to hydrolysis thereof and the corrosion of a container accommodating this compound. For the most efficient heat generation, it is desirable that calcium oxide be in the form of about 1- to about 20- mesh pieces or grains. Preferably the reaction between calcium oxide and water is initiated not immediately after the addition of the latter to the former but after the water added thereto has uniformly and satisfactorily permeated into calcium oxide pieces or grains. To retard the initiation of the exothermic reaction when calcium oxide comes into contact with water, the pieces or grains of calcium oxide can be coated with at least one of mineral oils, vegetable oils and fats, higher alcohols, polyhydric alcohols, higher fatty acids and derivatives thereof. The amount of water to be used is preferably about 0.2 to about 3 times the stoichiometric amount, and is for example about 0.2 to about 3 moles per mole of calcium oxide. When blowing agents which will evolve a gas at lower temperatures are used, diatomaceous earth, acid clay, zeolite or like clay can be added to the exothermic substance so as to regulate the heating time and temperature to be given by the heat evolved from the substance.

The mixture and the exothermic substance are accommodated in two respective compartments of a container as separated from each other by a partition providing a heat transfer surface. The container is provided with the mixture and the exothermic substance, or alternatively they are introduced in the container immediately before the use of the container. The container is made of heat resistant material such as an iron plate. The mixture and the exothermic substance can be contained in any desired arrangement within the container. The arrangements can be divided into three general types:

(i) Arrangement in which the mixture is positioned above the exothermic substance with a substantially horizontal partition interposed therebetween.
(ii) Arrangement in which the mixture and the exothermic substance are separated from each other by a substantially vertical partition.
(iii) Arrangement in which the mixture and the exothermic substance are separated from each other substantially horizontally and vertically.

In the arrangements (ii) and (iii), it is preferable to arrange the two components concentrically when seen in a plan view, with either one of the two positioned outside the other. In the case of concentric arrangement, the mixture may be accommodated in a plurality of separate compartments. Several kinds of mixtures having varying components and efficacies can be accommodated in the compartments respectively.

The mixture accommodating compartment has an open upper end which may be kept sealted until the apparatus is put into use. When a material which is meltable but is not burned with the heat evolved from the exothermic substance is used for sealing the compartment, there is no need to remove the seal by hand when using the apparatus, nor any likelihood of hand coming into contact with the mixture, hence convenient and safe. It is preferable that the meltable seal generally have a thickness of up to 200 microns and be melted but unburned by the heat evolved from the exothermic substance. Preferably the seal is made of materials having a melting point not higher than 250° C. Examples of useful sealing materials are films of various synthetic resins such as polyethylene, polyvinyl chloride, polyester, polycarbonate, polyamide, polyvinylidene chloride, etc.; cellophane film; acetate film; and multilayer films thereof such as cellophane-polyethylene film, polyvinylidene chloride coated polyester-polyethylene film, polyamide-polyethylene film, polyvinylidene chloride coated polyamide-polyethylene film, polypropylene-cellophane-polyethylene film, etc.

The meltable seal can be covered with another film or sheet for reinforcing the seal. The covering film or sheet has a number of perforations and may be made from metal such as iron, aluminum or alloy thereof, synthetic resin or paper.

The compartment for accommodating the exothermic substance may be optionally closed or opened, but is usually closed to eliminate heat losses. The closed compartment is provided with means for supplying water to the exothermic substance. For instance, the water supplying means is in the form of at least one water inlet aperture formed in an upper portion and/or lower portion of the closed compartment or comprises a water reservoir which can be opened from outside.

The water reservoir is made from a film of easily breakable material such as an aluminum foil or synthetic resin film.

Examples of means for opening the water reservoir from outside, although not particularly limited, are preferably as follows:

(i) A thread attached to the water reservoir and adapted to be pulled from outside to break the portion of the reservoir where the thread is attached.
(ii) A needle adapted to puncture the water reservoir when pushed into the container from outside.
(iii) A cutter provided within the container and displaceable from outside to cut the water reservoir.
(iv) One of the means (i) to (iii) which is so arranged as to cause the exothermic substance to contact part of the water contained in the reservoir, permitting the resulting heat to melt and break the meltable film which forms the water reservoir. The sealing materials exemplified above are usable for the meltable film.

When the means (ii) or (iii) is used, the closed compartment is provided with suitable means for restraining the needle or cutter from inadvertent displacement.

Preferably water can be applied to the exothermic substance in such a manner that water placed in the bottom of the container is introduced through water inlet apertures in a lower part of the container into a water-permeable layer provided in the closed compartment from which the water comes into contact with the exothermic substance. The water-permeable layer, when employed, allows water to be applied to the exothermic substance uniformly over an increased area for efficient heat generation. The seeping rate of the water through the layer is suitably adjustable by varying the density, material and thickness of the layer. When such a water-permeable layer forms the bottom wall of the closed compartment, water can be supplied to the exothermic substance without the necessity of forming water inlet apertures in the bottom wall. Alternatively a water-permeable layer impregnated with water and sealed with a meltable film may be provided within the closed compartment, preferably in combination with one of the opening means (i) to (iii) as already stated.

The water-permeable layer has numerous minute spaces as in open-cellular foamed materials and mats of fibrous material. The layer can be made from any water-permeable material. Examples of useful materials are woven and nonwoven fabrics of polyethylene, polypropylene, polyvinylidene chloride or like synthetic fibers, or of a blend of such synthetic fibers and cotton, mats of glass wool, asbestos, rock wool or like inorganic fibers, filter paper or like paper made of pulp, etc.

The exothermic substance filling the closed compartment swells on application of water and also raises the internal temperature of the compartment owing to the resulting heat generation to expand the air therein, so that the internal pressure of the container will build up to a very high level. Accordingly an opening for maintaining the internal pressure in balance with the atmospheric pressure can be formed in the wall defining the closed compartment.

When the exothermic substance evolves heat on application of water, the heat indirectly heats the mixture of blowing agent and active ingredient through the partition, thereby decomposing the blowing agent and vigorously volatilizing the active ingredient. According to this invention, the active ingredient can be very effectively volatilized in a large quantity within a short period of time, e.g. a few minutes or ten-odd minutes, presumably because the blowing agent mixed with the active ingredient gives off a gas on decomposition, forcing the active ingredient to volatilize promptly from the interior of the mixture and because the active agent per se remains free of decomposition due to combustion. The apparatus of this invention, which are capable of very efficiently and quickly releasing large quantities of vapors of active ingredients, are useful in controlling noxious insects, such as flies, mosquitoes, fleas, bed bugs, house ticks and cockroaches, which are detrimental to man, as well as plant lice, green house whiteflies, caterpillars and other insects which are harmful to agricultural plants, and are also serviceable for fungicidal and incensing purposes. Additionally the present apparatus are usable for these applications with high safety and great convenience substantially without involving combustion which would produce smoke with toxicity and a pungent odor and without necessitating any igniting means or power supply whatsoever.

This invention will be described below in greater detail with reference to the preferred embodiments shown in the accompanying drawings, in which.

Figure 1:
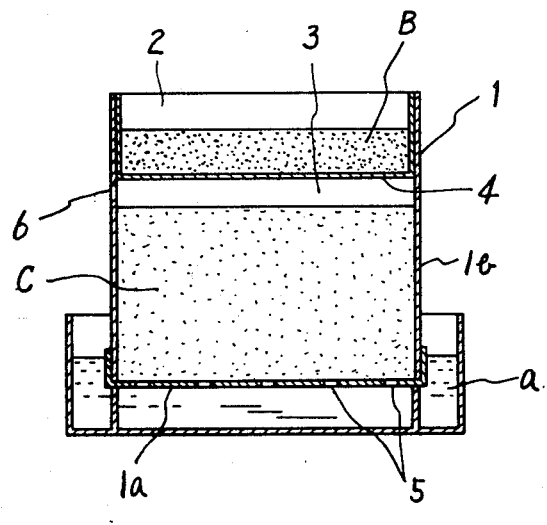
FIG. 1 is a view in vertical section showing an embodiment of the invention in which the bottom wall of a container is formed with water inlet apertures.
Figure 2:
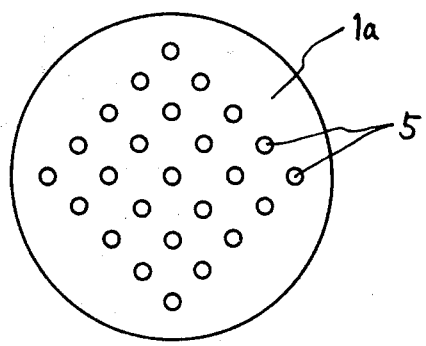
FIG. 2 is a bottom view showing the water inlet apertures of the container shown in FIG. 1.
Figure 3:
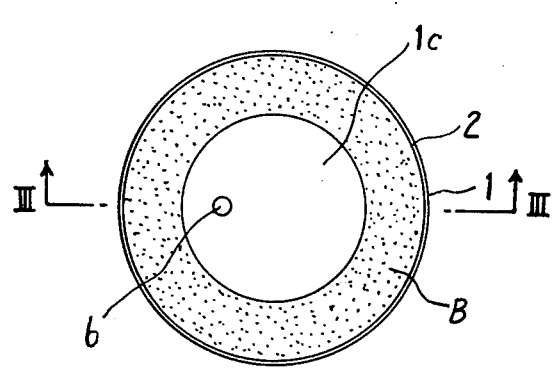
Figure 15:
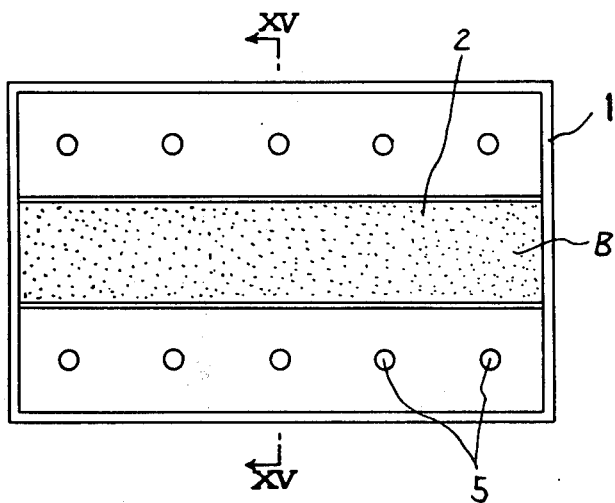
Figure 16:
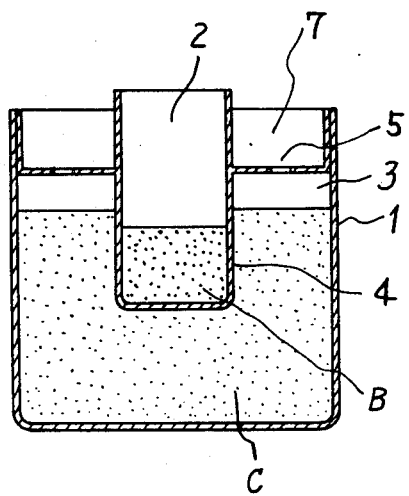
Figure 17:
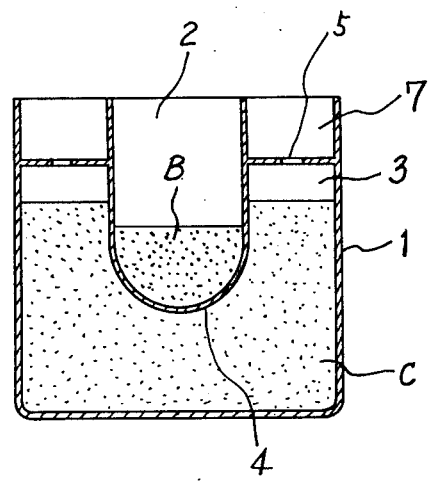
Figure 18:
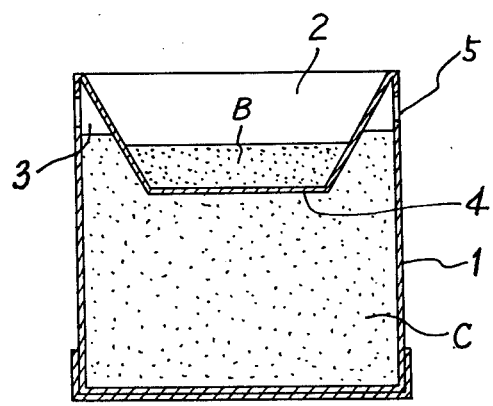
Figure 19:
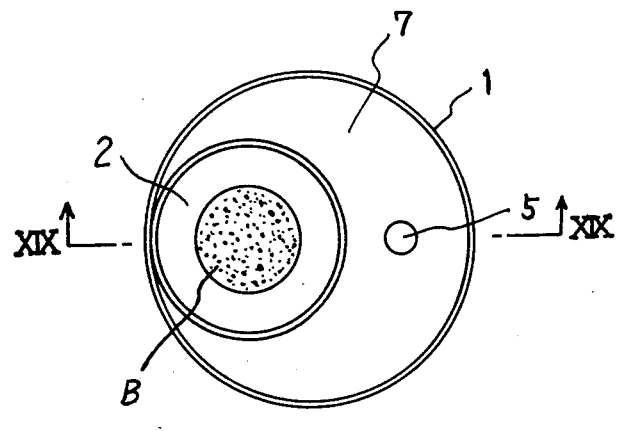
Figure 20:
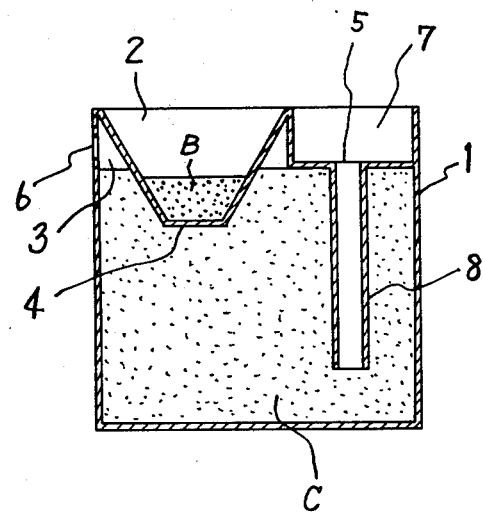
Figure 21:
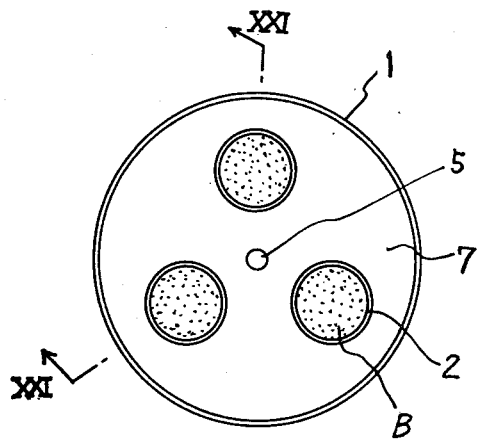
Figure 22:
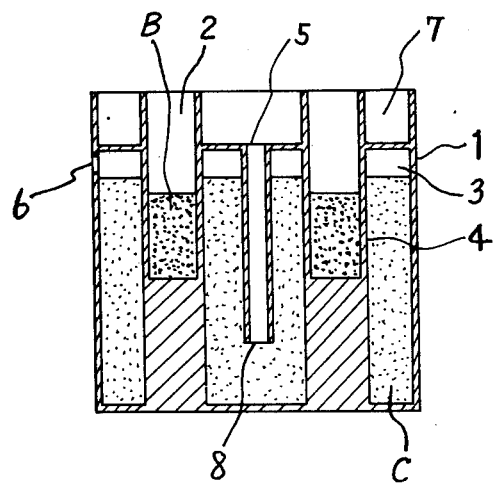
Figure 23:
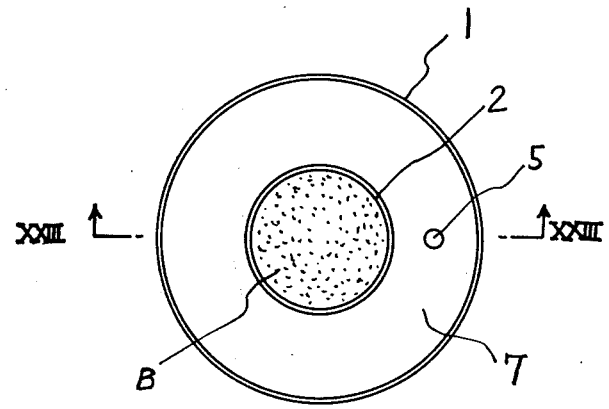
Figure 24:
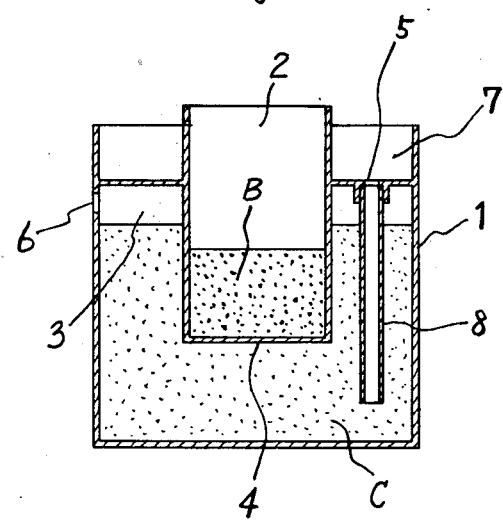
Figure 35:
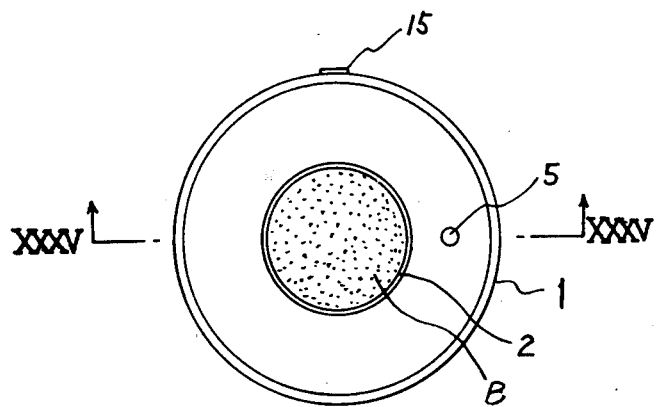
Figure 36:
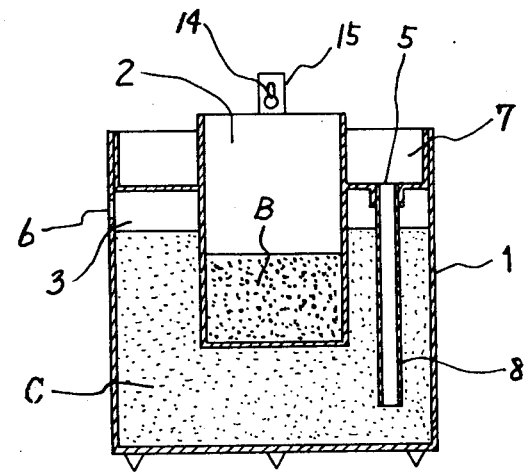
Figure 37:
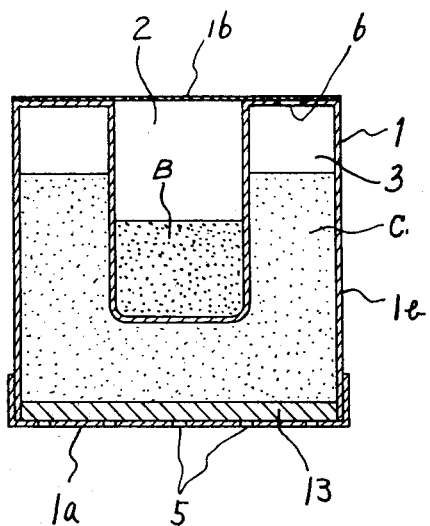
Figure 38:
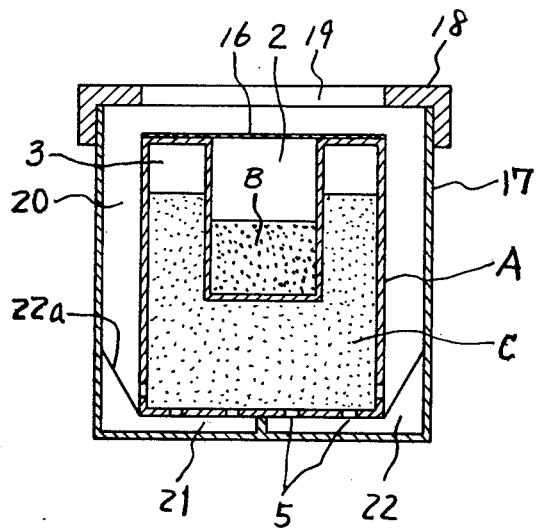
Figure 39:
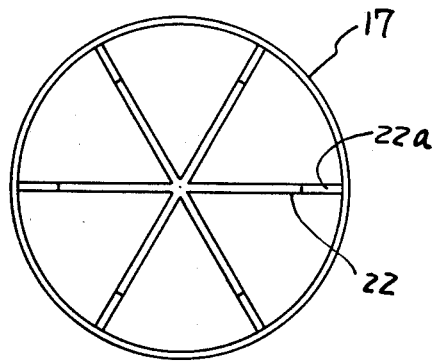
Figure 40:
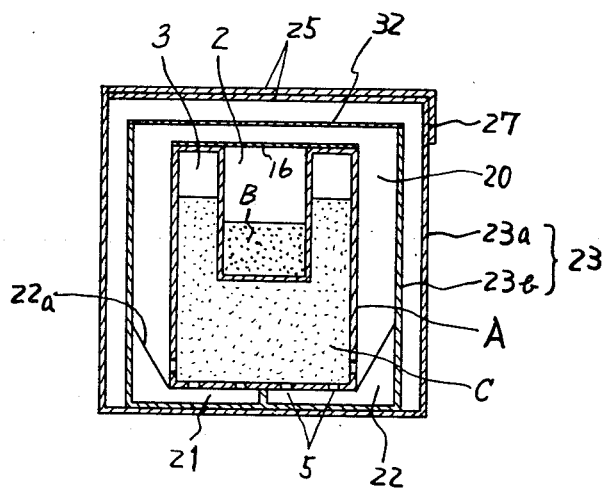
Figure 42:
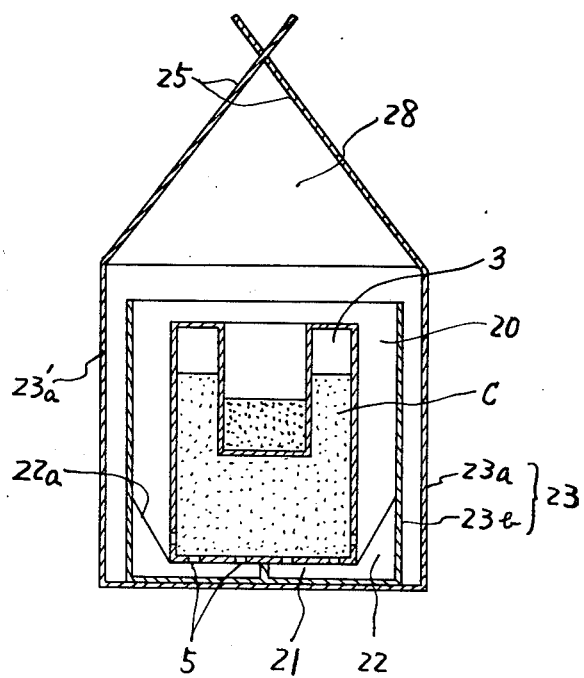
Figure 41:
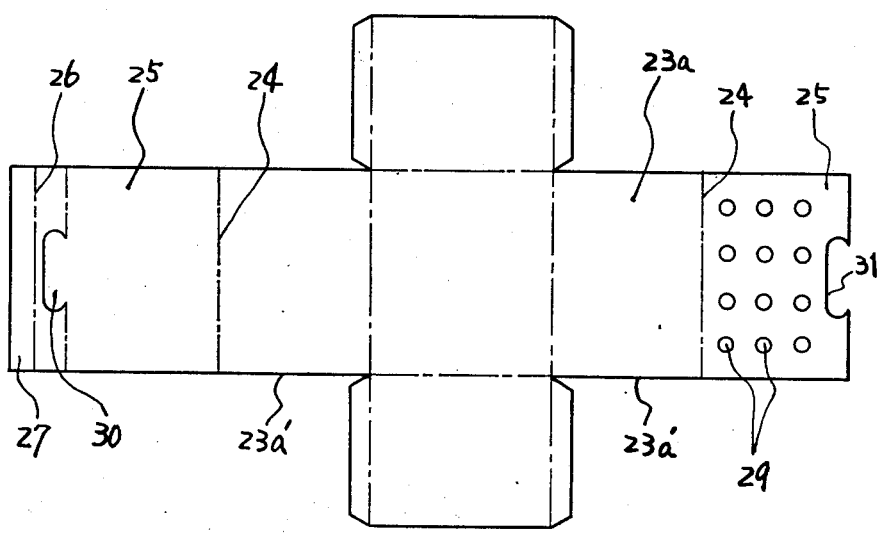

FIGS. 3 and 4, FIGS. 5 and 5A, FIGS. 6 and 7, FIGS. 8 and 9, FIGS. 10 and 11, and FIGS. 12 and 12A are plan views and vertical sections respectively taken on lines III—III, V—V, VI—VI, VIII—VIII, X—X, and XII—XII which show embodiments of this invention comprising a container having the same water supplying means as in the embodiment of FIGS. 1 and 2;

FIGS. 13 and 14, and FIGS. 15 and 16 are plan views and vertical sections respectively taken on lines XIII—XIII and XV—XV which show embodiments of this invention comprising a container with at least one water inlet aperture formed in its upper portion;

FIG. 17 and FIG. 18 are vertical sections showing modifications of the embodiment illustrated in FIGS. 15 and 16;

FIGS. 19 and 20, FIGS. 21 and 22, and FIGS. 23 and 24 are plan views and vertical sections taken on lines XIX—XIX, XXI—XXI and XXIII—XXIII which show embodiments of this invention comprising a container having in its top portion a water inlet aperture provided with a water inlet tube;

FIG. 25, FIG. 26, FIG. 27 and FIG. 28 are views in vertical section each showing an embodiment of this invention in which a container incorporates a water reservoir;

FIG. 29, FIG. 30, FIG. 31, FIG. 32, FIG. 33 and FIG. 34 are views in vertical section each showing an embodiment of this invention in which water is supplied to an exothermic substance through a water-permeable layer;

FIGS. 35 and 36 are a plan view and a view in vertical section taken on lines XXXV—XXXV which show an embodiment of this invention in which a container is porvided with means for attaching the apparatus to a wall, column, ceiling and the like;

FIG. 37 is a view in vertical section showing an embodiment of this invention in which a compartment accommodating a mixture of active ingredient and blowing agent is sealed with a meltable film;

FIGS. 38 and 39 are a view in vertical section and a plan view showing a preferred case for enclosing the apparatus of this invention;

FIG. 40 is a view in vertical section showing another preferred case for enclosing the apparatus of this invention;

FIG. 41 is a plan view in development showing the case;

FIG. 42 is a view in vertical section showing the case during use; and

Figure 43:
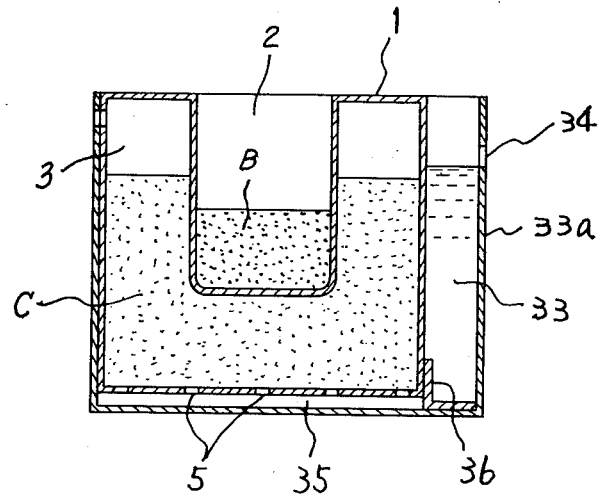
Figure 44:
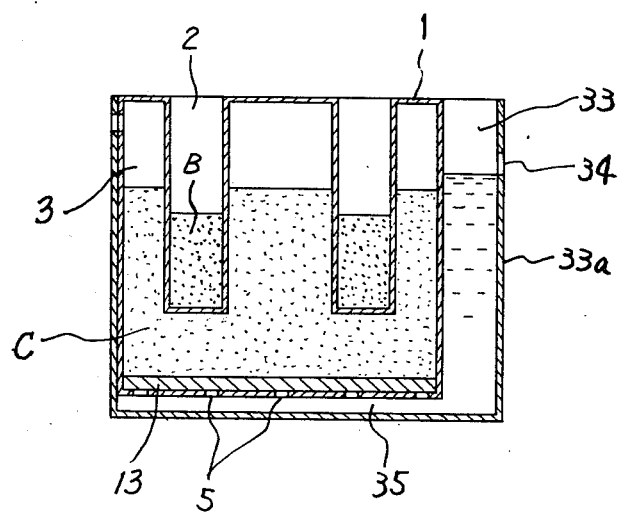
Figure 45:
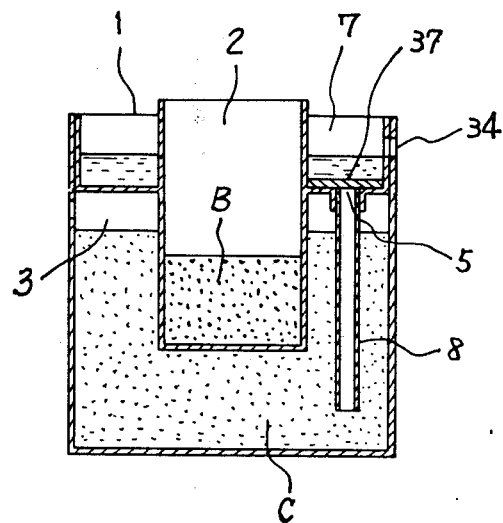

FIG. 43, FIG. 44 and FIG. 45 are views in vertical section each showing an embodiment of this invention provided with means for supplying a specified amount of water.

FIGS. 1 and 2, FIGS. 3 and 4, FIGS. 5 and 5A, FIGS. 6 and 7, FIGS. 8 and 9, FIGS. 10 and 11, and FIGS. 12 and 12A respectively show embodiments of this invention each comprising a container 1 with water inlet apertures 5 formed in its bottom wall 1a. The heating element is formed of an exothermic substance which evolves heat on contact with water.

The container 1 of FIGS. 1 and 2 accommodates a mixture B of an active ingredient and a blowing agent in its upper open compartment 2 and an exothermic substance C in its lower closed compartment 3 separated from the mixture B by a partition 4. In FIGS. 3 and 4 and FIGS. 5 and 5A, the mixture B and the substance C contained in the container 1 are separated from each other by a vertical partition. The mixture B and the exothermic substance C shown in FIGS. 6 and 7, and FIGS. 8 and 9 are accommodated in the container 1 as vertically and horizontally separated from each other, with the mixture B placed at an upper position of the substance C.

In FIGS. 10 and 11, and FIGS. 12 and 12A, the mixture B is accommodated in the open compartment 2 of the container 1 as divided into a plurality of small portions, in which case the portions need not always be of the same kind, but several kinds of mixtures B of varying compositions and efficacies may be contained separately.

When the bottom of the container 1 is placed in water a in use of the apparatus shown in FIGS. 1–12A, the water enters the closed compartment 3 through the water inlet apertures 5 in the bottom wall 1a thereof and comes into contact with the exothermic substance C contained therein, causing the substance to evolve heat. The heat indirectly heats the mixture B in the open compartment 2 of the container 1 through the partition 4, thereby decomposing the blowing agent in the mixture B and vigorously volatilizing the active ingredient.

On absorbtion of water, the exothermic substance C increases its volume and gives off heat to expand the air in the compartment 3, increasing the internal pressure of the closed compartment 3 and impeding smooth ingress of the water through the inlet apertures 5. Uneven heat generation will then result. It is therefore desirable that the container 1 be formed, in its side wall 1b or top wall 1c, with a balance opening 6 for maintaining the interior of the closed compartment 3 in communication with the atmosphere.

Figure 4:
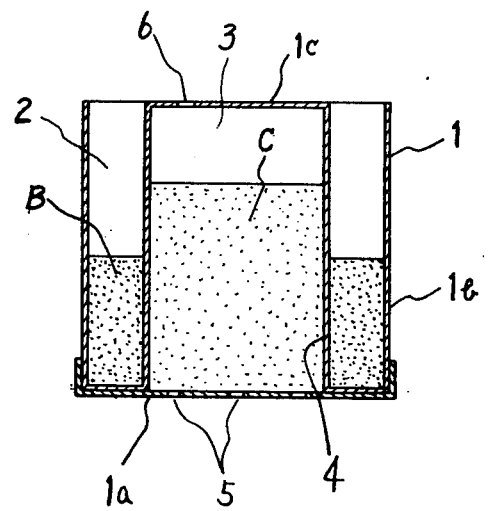
Figure 5A:
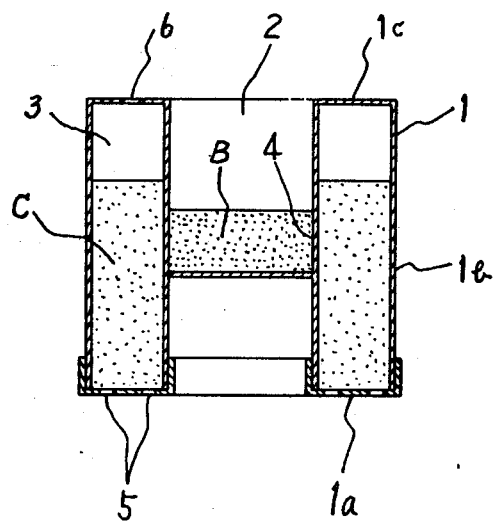
Figure 5:
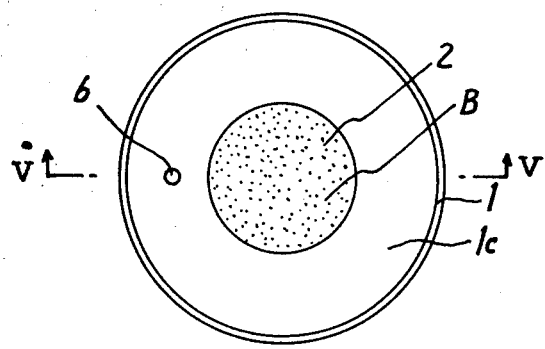
Figure 6:
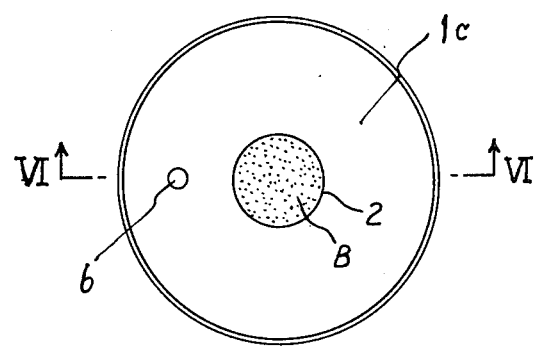
Figure 7:
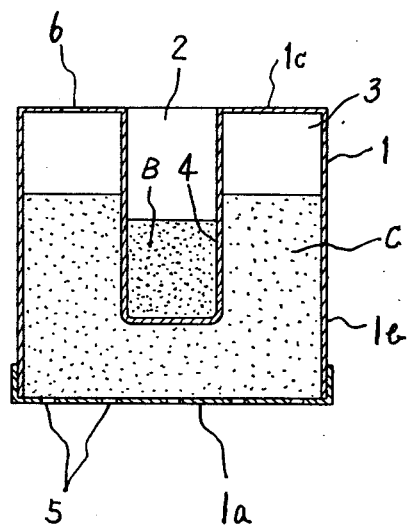
Figure 8:
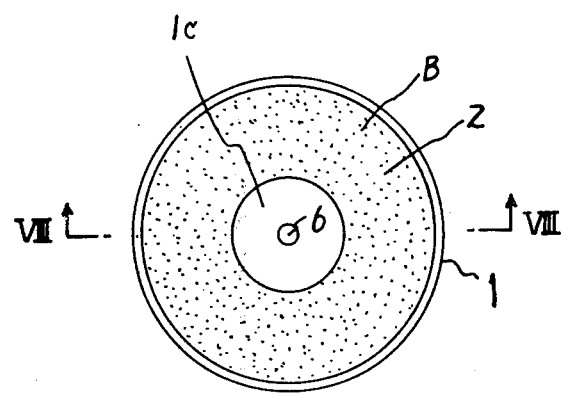

As seen in FIGS. 1 and 4, the bottom wall 1a of the container 1 is preferably detachable for use with a refill of the exothermic substance.

Figure 9:
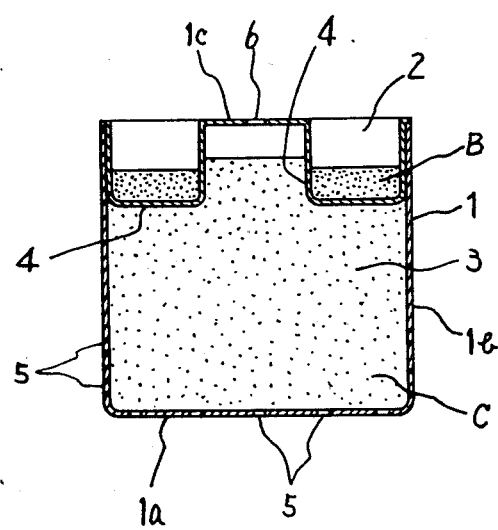
Figure 10:
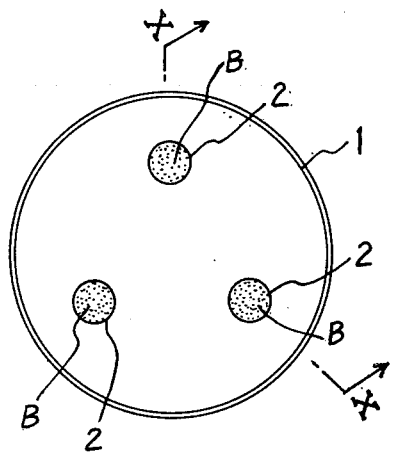
Figure 11:
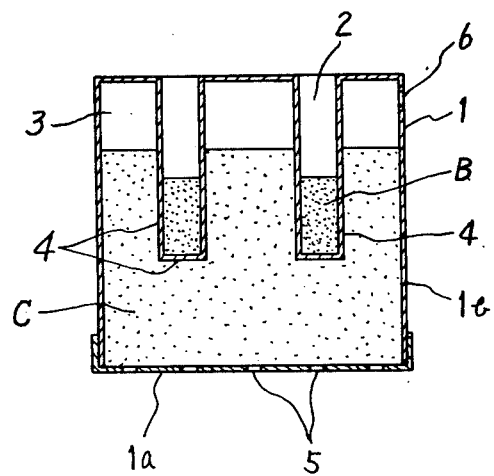
Figure 12:
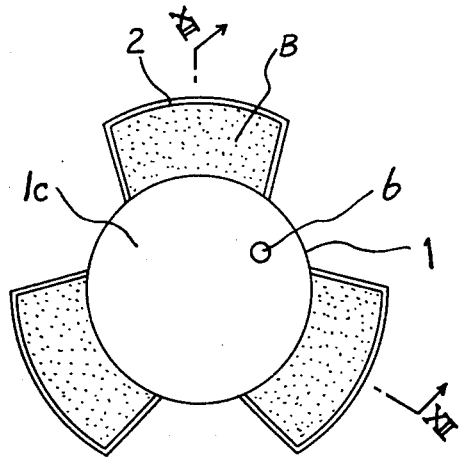
Figure 12:
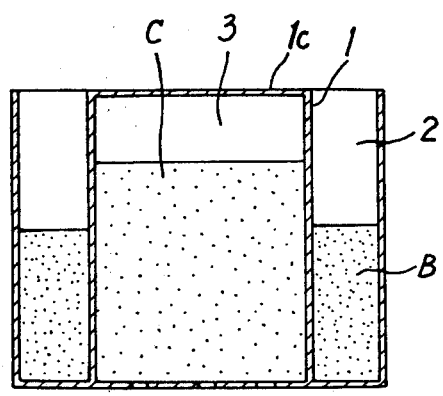
Figure 13:
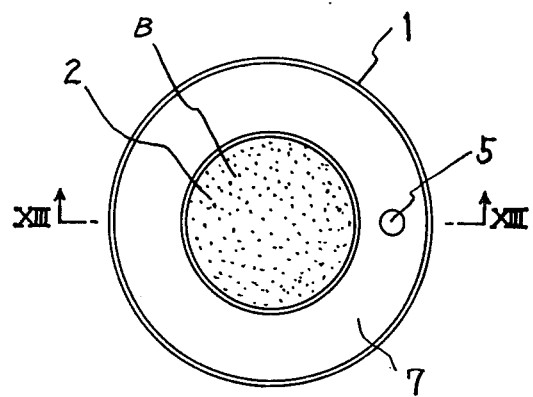

FIG. 9 shows water inlet apertures 5 formed in the bottom wall 1a and lower portion of the side wall 1b of the container 1.

FIGS. 13 and 14, and FIGS. 15 and 16 respectively show other embodiments of this invention each comprising a container 1 with at least one water inlet aperture 5 formed in the upper portion of its enclosed compartment 3.

These embodiments need not be provided with the above-mentioned balance opening, since the water inlet aperture 5 is serviceable also as such.

Figure 14:
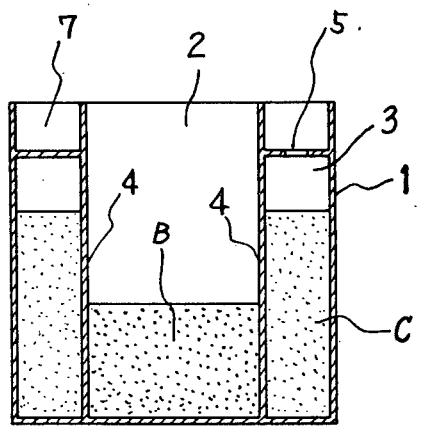

As shown in FIGS. 14 and 16, preferably a water receptacle 7 is provided in the upper portion of the container and the water inlet aperture 5 is formed in the bottom of the water receptacle 7.

FIGS. 17 and 18 show modifications of the embodiment illustrated in FIG. 15. The modifications of FIGS. 17 and 18 are substantially the same as the embodiment of FIG. 15 except that the partition of FIG. 17 has a curved lower part, while that of FIG. 18 has inclined side parts.

FIGS. 19 and 20, FIGS. 21 and 22, and FIGS. 23 and 24 respectively show other embodiments of this invention each comprising a container 1 having in its top portion a water inlet aperture 5 provided with a water inlet tube 8.

The water inlet tube 8 extends almost to the bottom of the container 1 to supply water to a bottom portion of an exothermic substance C filling a closed compartment 3 of the container 1. This arrangement enables the exothermic substance C to start heat generation at the bottom portion. For example, when water is supplied according to the embodiment of FIGS. 13 and 14 to the exothermic substance C through the water inlet aperture 5 in the upper part of the container 1, heat generation is initiated at the upper part of the exothermic substance C, and the water thus heated is partly vaporized, thereby involving a loss of water. Consequently the lower part of the exothermic substance might possibly remain without evolving heat. The use of the water inlet tube 8 prevents such undesirable loss of water, thus ensuring complete consumption of the substance for heat generation without any waste.

FIGS. 25 to 28 respectively show other embodiments of this invention in each of which a water reservoir 9 is incorporated in a closed compartment 3 of a container 1. The water reservoir 9 contains a sufficient amount of water required for the heat generation of an exothermic substance C.

Figure 25:
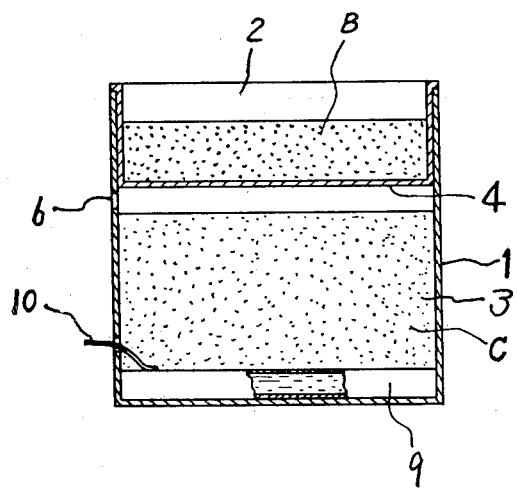
Figure 26:
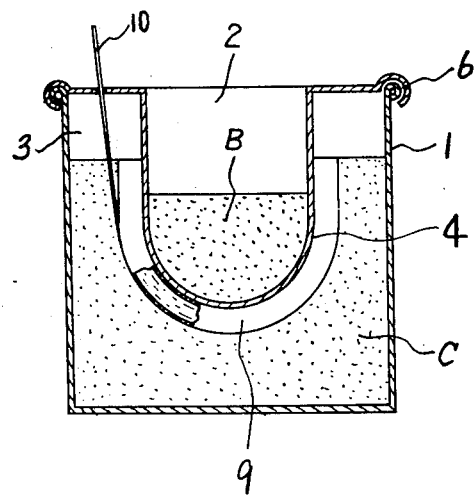
Figure 27:
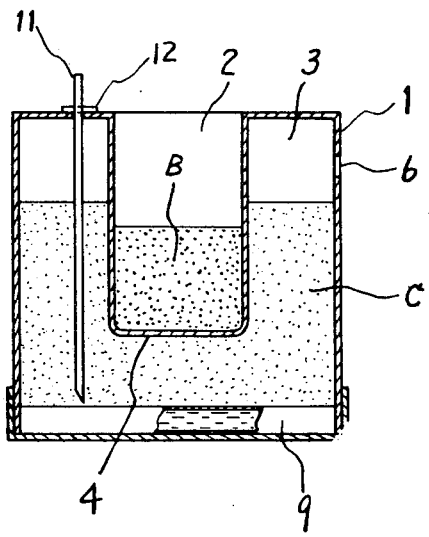
Figure 28:
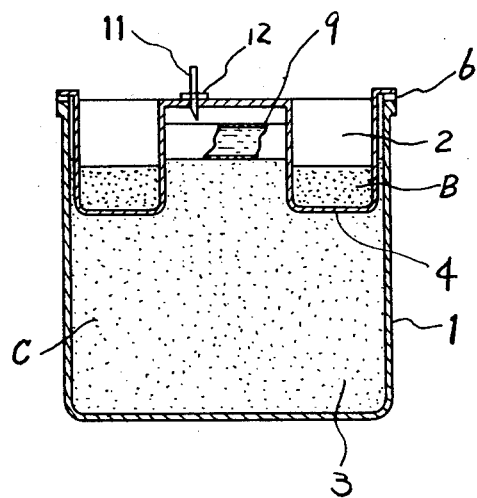

The embodiments of FIGS. 25 and 26 have a thread 10 which can be pulled from outside to break the water reservoir 9 when so desired, and those of FIGS. 27 and 28 have a needle 11 for puncturing the water reservoir 9 and a pin 12 for retaining the needle 11 in position. The pin 12 is removably inserted in the hole (not shown) of the needle 11. When the pin 12 is removed, the needle 11 is freely movable upward or downward.

FIG. 26 shows a balance opening 6 formed in an upper end peripheral curled portion of the container 1.

FIGS. 29 to 34 respectively show other embodiments of this invention which are so adapted that water is supplied to an exothermic substance C through a water-permeable layer 13.

Figure 29:
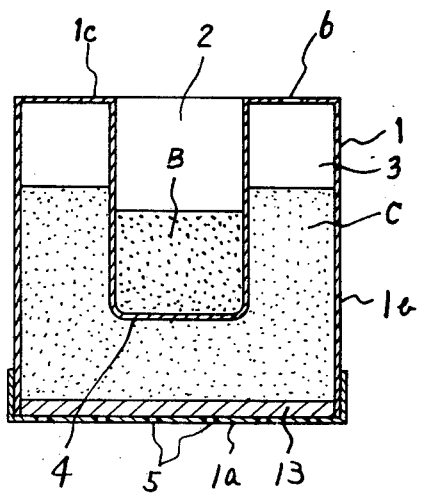
Figure 30:
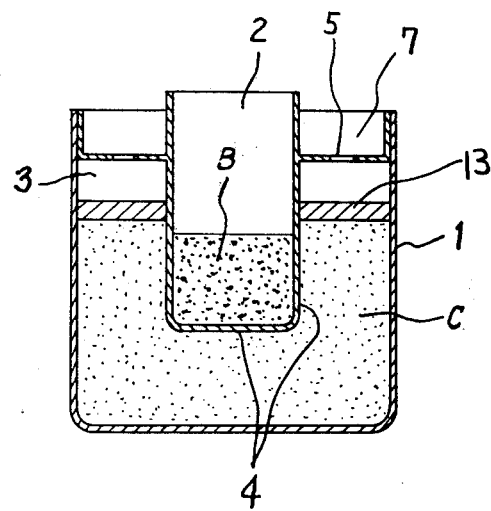
Figure 31:
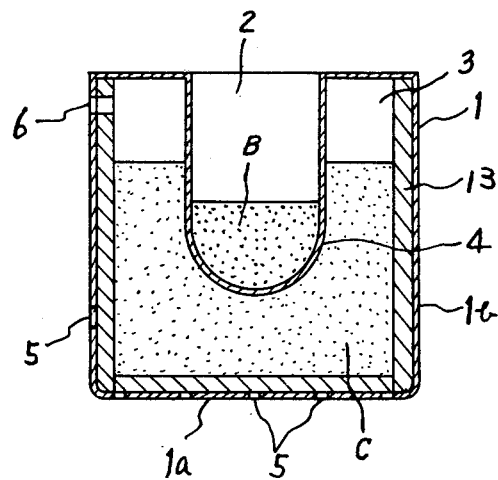

With the embodiments of FIGS. 29 to 31, the water supplied through water inlet apertures 5 seeps through the water-permeable layer 13 and comes into contact with the exothermic substance C to cause the substance C to evolve heat. Since the water seeps through the layer 13 over the entire surface area thereof, this arrangement assures very efficient heat generation.

When the water inlet apertures 5 are formed in the bottom wall 1a or lower portion of the side wall 1b of the container 1 as shown in FIGS. 29 and 31, the water-permeable layer 13 separates the exothermic substance C from the water inlet apertures 5, preventing the substance C from falling through the apertures 5, so that the water inlet apertures 5 can be of relatively large diameter.

Figure 32:
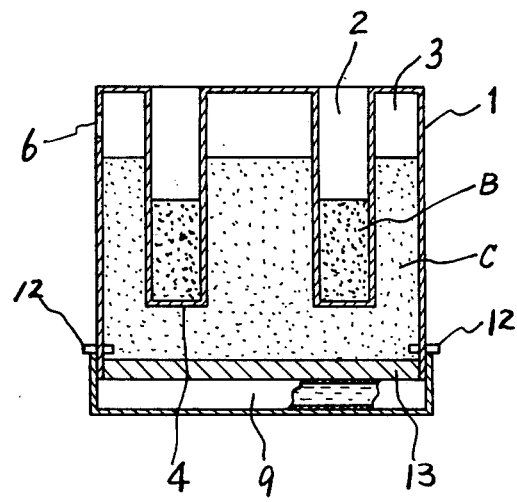
Figure 33:
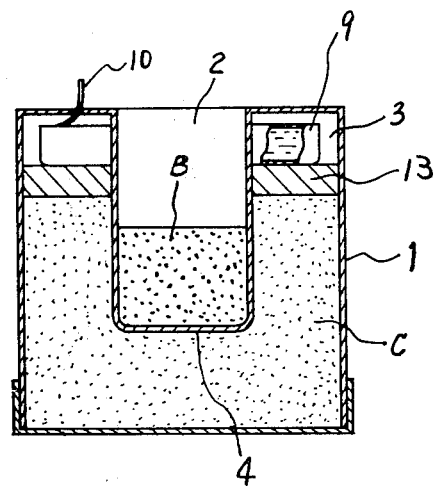
Figure 34:
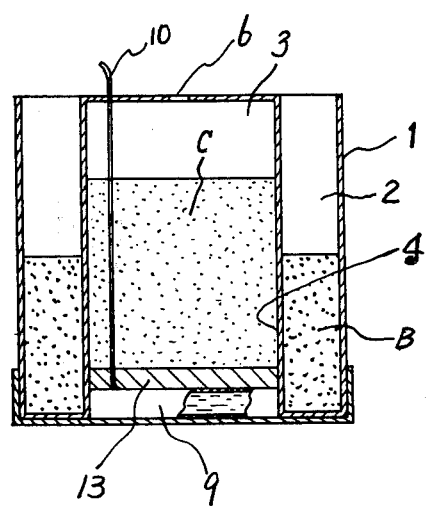

FIGS. 32 to 34 show embodiments of the type in which water is supplied from a water reservoir 9 to a water-permeable layer 13. With the embodiment of FIG. 32, the main body of a container 1 is depressed, with retaining pins 12 removed, to break the water reservoir 9 for the application of water to the layer 13. With the embodiments of FIGS. 33 and 34, a thread 10 is pulled to break the reservoir 9.

FIGS. 35 and 36 sbow another embodiment of this invention including a container 1 which is mountable on a vertical wall, column, ceiling and other. The container 1 has a lug 15 projecting from its upper end periphery and having a hole 14. A hook (not shown) on a wall, column, ceiling or the like is engageable in the hole 14 to support the container.

FIG. 37 shows another embodiment of this invention in which a compartment accommodating a mixture B has an open end which is sealed with a meltable film 16. The film 16 is removable by being melted with the heat evolved from an exothermic substance C and the heat of the gas released from an active ingredient with that heat. The apparatus of this type is convenient to use since the seal over the mixture accommodating compartment need not be separated before use.

FIGS. 38 and 39, and FIGS. 40 to 42 respectively show preferred cases for enclosing an apparatus A according to this invention of the type in which water inlet apertures 5 are formed in the bottom wall 1a of a container 1. When opened, the case 17 (23) is usable as a container for water.

With reference to FIGS. 38 and 39, a cover 18 is detachable from the case 17. The cover 18 is detached from the case when water is introduced into the case. The cover 18 is refixed to the case 17 after the supply of water. The cover 18 has an opening 19 serving as a passage for the vapor given off from the mixture B in the open compartment 2.

The case 17 and the apparatus A enclosed therein define an annular space 20 which serves as a heat insulating portion for protecting the case 17 from the heat evolved from the exothermic substance C.

The case 17 has projections 22 of small width provided on its bottom and extending radially from the center thereof. The projections 22 support the apparatus A thereon and form spaces 21 beneath the apparatus A, the spaces 21 serving to accommodate the water to be supplied to the apparatus A through the water inlet apertures 5 in the bottom of the apparatus. The projections 22 each have an upwardly outwardly sloping top face 22a, rendering the apparatus accurately positionable within the case 17 concentrically therewith.

The case 23 shown in FIGS. 40 to 42 is of the same construction as the case 17 except that the case 23 comprises an outer case member 23a of the knockdown type and a plastics inner case member 23b disposed within the outer case member 23a concentrically therewith.

FIG. 41 is a development showing the outer case member 23a. The top cover portion thereof comprises cover pieces 25, 25 extending from the upper ends of the opposite side walls 23a', 23a' of the outer case member 23a with folds 24, 24 formed therebetween. One of the cover pieces 25 further extends outward into an attaching piece 27 with a perforated fold 26 formed at the outer end of the cover piece.

When the present apparatus is to be used, the cover pieces 25, 25 are unfolded to a semi-open position as shown in FIG. 42. In this state, openings 28, 28 are formed on the opposite sides of the cover pieces 25, 25. The vapor released from the apparatus is diffused into the outside atmosphere through the openings 28, 28. To ensure more efficient diffusion, one of the cover pieces 25 can be formed with holes 29 (see FIG. 41). To retain the cover pieces 25 in a semi-open position, one of the opposed ends of the cover pieces has a tongue-like insert piece 30 and the other end a cutout 31 for receiving the insert piece 30.

As seen in FIG. 40, the inner case member 23b has a seal 32 closing its open upper end. The seal 32 is removed when the apparatus is put to use.

FIG. 43, FIG. 44 and FIG. 45 are views in vertical section each showing an embodiment of this invention provided with means for supplying a specified amount of water.

With reference to FIG. 43, a container 1 is provided on one side thereof with a water receptacle 33. An overflow opening 34 is formed in the outer wall 33a of the receptacle 33 at a suitable level. The lower end of the receptacle 33 communicates with a slit 35 provided beneath the bottom of the container 1. The bottom of the container 1 has water inlet aperture 5 opened to the slit 35. The portion where the lower end of the water receptacle 33 communicates with the slit 35 is provided with a seal 36 which is opened after water has been placed into the receptacle 33. When made of water-soluble material, the seal 36 is openable without being opened by hand.

When the level of the water placed into the receptacle rises beyond the overflow opening 34, excess water flows out from the opening 34, with the result that a predetermined amount of the water remains in the receptacle 33. The seal 36 is thereafter removed, permitting the water to enter the slit 35 from the lower end of the receptacle 33 and to flow into the container 1 via the water inlet apertures 5 opened to the slit 35.

When a water-permeable layer 13 of suitably selected material is provided on the bottom of a container 1 as seen in FIG. 44, the layer 13 also has substantially the same function as the seal 36 shown in FIG. 43, thus eliminating the necessity of providing a seal between the water receptacle 33 and the slit 35.

FIG. 45 shows a container 1 having in its top portion a water receptacle 7 the side wall of which is formed with an overflow opening 34 for ensuring the supply of a specified amount of water. The receptacle 7 has a water inlet aperture 5 which is closed with a seal 37. The seal 37 is removed after the specified amount of water has been placed into the receptacle 7.

In the embodiments shown in FIGS. 43 to 45, a line indicating a specified level of water may be drawn on the outer wall 33a of the receptacle 33 of the container, instead of forming the foregoing overflow opening 34.

Throughout FIG. 1 to FIG. 45, like numerals indicate like members. A supply of water to the exothermic substance in the closed compartment according to the embodiments of FIGS. 13 to 45 achieves substantially the same results as with the embodiments of FIGS. 1 to 12A.

This invention will be described below in greater detail with reference to examples, in which the effective fugacity rates of active ingredients are determined by volatilizing the ingredient within a closed container, passing the air within the container through a solvent which completely dissolves the active ingredients, such as benzene, acetone, water, chloroform or dichloromethane to cause the solvent to absorb the vaporized ingredient in the air, concentrating the solvent and subjecting the concentrate to gas chromatography. The fugaicty rate is expressed in terms of the ratio in percent of the quantity of the active ingredient to the quantity of the ingredient initially admixed with a blowing agent.

EXAMPLE 1

A mixture of an insecticide and a blowing agent as listed in Table 2 is placed into an apparatus of this invention utilizing 100 g of calcium oxide (1-to 5-mesh pieces) and shown in FIG. 29. The apparatus is brought to contact with water and 40 g of water enters into a compartment accommodating calcium oxide via inlet apertures in its bottom wall to heat the mixture to a temperature of up to about 300° to about 350° C. with the resulting heat, whereby the blowing agent is thermally decomposed to volatilize the insecticide. The effective fugacity rate of the insecticide is determined.

The results are shown in Table 2.

Table 2

| Specimen No. | Insecticide | (g) | Blowing agent | (g) | Effective fugacity rate (%) |
|---|---|---|---|---|---|
| 1 | allethrin B | 1 | AIBN | 5 | 69.4 |
| 2 | DDVP | 1 | TSH | 10 | 61.1 |
| 3 | " | 1 | 2,4-TSH | 10 | 63.0 |
| 4 | " | 1 | OSH | 10 | 74.2 |
| 5 | allethrin A | 1 | AZ-A | 10 | 69.1 |
| 6 | " | 1 | AZ-B | 10 | 65.6 |
| 7 | " | 1 | CIB | 10 | 61.6 |
| 8 | " | 1 | ACHC | 10 | 63.2 |
| 9 | allethrin B | 1 | AC | 1 | 65.3 |
| 10 | " | 1 | AC | 3 | 74.9 |
| 11 | " | 1 | AC | 5 | 86.7 |
| 12 | allethrin A | 1 | AZ-B | 10 | 63.0 |
| 13 | DDVP | 1 | OSH | 10 | 70.1 |
| 14 | allethrin A | 1 | CIB | 10 | 60.5 |

Table 2-continued

| Specimen No. | Insecticide | (g) | Blowing agent | (g) | Effective fugacity rate (%) |
|---|---|---|---|---|---|
| 15 | allethrin B | 1 | AC | 1 | 60.8 |
| 16 | " | 1 | AC | 3 | 72.9 |
| 17 | resmethrin | 1 | AC | 5 | 83.4 |
| 18 | " | 0.5 | AC | 2 | 75.0 |
| 19 | " | 0.5 | AC | 4 | 84.0 |
| 20 | " | 0.5 | AC | 5 | 82.3 |
| 21 | " | 0.5 | AC | 10 | 79.8 |
| 22 | " | 0.5 | DPT | 1.5 | 80.8 |
| 23 | phthalthrin | 0.5 | AC | 5 | 63.0 |
| 24 | phenothrin | 0.5 | AC | 5 | 75.5 |
| 25 | permethrin | 0.5 | AC | 5 | 78.1 |
| 26 | DDVP | 0.5 | AC | 4 | 78.2 |
| 27 | resmethrin | 1 | AC / AZ-B | 1 / 1 | 65.2 |
| 28 | allethrin B | 1 | AC / AIBN | 1 / 1 | 68.1 |

COMPARATIVE EXAMPLE 1

The same procedure as in Example 1 is repeated without using any blowing agent. Table 3 shows the results.

Table 3

| Specimen No. | Insecticide | (g) | Blowing agent | (g) | Effective fugacity rate (%) |
|---|---|---|---|---|---|
| 29 | resmethrin | 1 | — | — | 0.3 |
| 30 | allethrin B | 1 | — | — | 0.7 |

COMPARATIVE EXAMPLE 2

To a cylindrical container with a single compartment accommodating 100 g of calcium oxide conjointly with an insecticide only or with an insecticide and a blowing agent listed in Table 4 is supplied 40 g of water in the same manner as in Example 1 to determine the effective fugacity rate achieved. Table 4 shows the results.

Table 4

| Specimen No. | Insecticide | (g) | Blowing agent | (g) | Effective fugacity rate (%) |
|---|---|---|---|---|---|
| 31 | resmethrin | 1 | — | — | 0.2 |
| 32 | allethrin B | 1 | — | — | 0.3 |
| 33 | resmethrin | 1 | AC | 5 | 4.2 |
| 34 | allethrin B | 1 | AC | 5 | 5.1 |

COMPARATIVE EXAMPLE 3

The mixtures listed in Table 5 each composed of an insecticide and a combustible material as in known fumigants, were burned for fumigation. Table 5 also shows the effective fugacity rates achieved.

Table 5

| Specimen No. | Insecticide | (g) | Combustible material | (g) | Effective fugacity rate (%) |
|---|---|---|---|---|---|
| 35 | resmethrin | 0.5 | nitrocellulose (30%) | 30 | 6.3 |
| 36 | allethrin B | 0.5 | " | 30 | 1.7 |
| 37 | phthalthrin | 0.5 | " | 30 | 7.2 |
| 38 | phenothrin | 0.5 | " | 30 | 8.1 |
| 39 | permethrin | 0.5 | " | 30 | 8.6 |

Tables 2 to 5 show that the method of this invention using present apparatus can achieve remarkably improved effective fugacity rate.

EXAMPLE 2

The same procedure as used in Example 1 is repeated with the exception that a blowing agent containing an additive is used as shown in Table 6. The results are also given in Table 6.

Table 6

| Specimen No. | Insecticide | (g) | Blowing agent | (g) | Effective fugacity rate (%) |
|---|---|---|---|---|---|
| 40 | resmethrin | 1 | CELLMIC CAP* | 5 | 86.8 |
| 41 | " | 0.5 | CELLMIC AN** | 5 | 87.5 |

*"CELLMIC CAP" is a AC-type blowing agent manufactured by SANKYO KASEI CO., LTD., Japan.
**"CELLMIC AN" is a blowing agent manufactued by the same company and containing a mixture of 50% DPT and 50% urea as an additive.

Table 6 reveals that the use of the additive with the blowing agent achieves the results as excellent as those shown in Table 2.

EXAMPLE 3

The same procedure as used in Example 1 is repeated except that to the active ingredient is added a synergist (for Specimens No. 42 to No. 46), a deordorant or perfume (for Specimens Nos. 47 and 48) or a fugacity rate improving agent (for Specimens Nos. 49 and 50) as shown in Table 7, which also shows the results.

Table 7

| Specimen No. | Insecticide | (g) | Additive | (g) | Blowing agent | (g) | Effective fugacity rate (%) |
|---|---|---|---|---|---|---|---|
| 42 | resmethrin | 1 | S-421 | 2 | AC | 3 | 79.4 |
| 43 | " | 1 | piperonyl butoxide | 3 | " | 5 | 85.8 |
| 44 | " | 1 | Lethane 384 | 3 | " | 5 | 85.5 |
| 45 | " | 1 | Cynepirine-222 | 3 | " | 5 | 87.7 |
| 46 | " | 1 | Cynepirine-500 | 3 | " | 5 | 86.2 |
| 47 | " | 0.5 | citral | 0.1 | " | 2 | 82.4 |
| 48 | " | 0.5 | LMA | 0.1 | " | 1 | 78.1 |
| 49 | " | 0.5 | phenethyl-isothiocyanate | 1 | CELLMIC AN | 5 | 90.3 |
| 50 | " | 0.5 | dimethyl ester of himic acid | 1 | CELLMIC AN | 5 | 89.6 |

Table 7 shows that the use of the additive with the active ingredient achieves the results as excellent as those shown in Table 2.

EXAMPLE 4

The same procedure as used in Example 1 is repeated except that a heat generation regulating agent listed in Table 8 is added to the calcium oxide. Table 8 also shows the results.

Table 8

| Specimen No. | Insecticide | (g) | Blowing agent | (g) | Heat generation regulating agent | (g) | Effective fugacity rate (%) |
|---|---|---|---|---|---|---|---|
| 51 | resmethrin | 1 | AC | 5 | zeolite | 5 | 87.4 |
| 52 | " | 1 | " | 5 | acid clay | 10 | 88.5 |
| 53 | " | 1 | " | 5 | diatomaceous earth | 10 | 88.2 |

Apparatus of the invention are tested for the quantity of smoke evolved, toxicity and insecticidal effect.

Quantity of smoke (turbidity)

An apparatus of this invention accommodating the same mixture as Specimen No. 20 is used in a chamber 90 cm×90 cm×90 cm to volatilize the active ingredient. For comparison, a fumigating composition composed of 30 g of a combustible material and 1.5 g of DDVP is burned in the same chamber as above.

The chamber is transparrent in the upper part and is lit up with a fluorescent light (20 w) provided in the upper center of the chamber. A marking plate is horizontally disposed in vertically movable manner in the chamber. The marking plate is a white disc made of plastic with a diameter of 35 mm. On the disc are drawn four black lines 0.5 mm in width such that two pairs of lines are intersected at a right angle in the center of the disc, two lines of each pair being spaced in parallel with a distance of 1.0 mm. The above disc is vertically moved to measure the longest distance (h) between the top of the chamber and the disc at which the four lines on the disc are clearly seen with unaided eyes. In this way, a turbidity within the chamber is calculated by the following equation:

$$\text{Turbidity (\%)} = \frac{h \text{ (cm)}}{90 \text{ (cm)}} \times 100$$

The same procedure is repeated five times for each specimen, giving the following average data.

|  | distance(cm) | turbidity(%) |
|---|---|---|
| Present invention | 67 | 74.4 |
| Comparison: | 16 | 17.8 |

The results indicate that the quantity of smoke emitted from the apparatus of this invention is substantially negligible.

Toxicity

A toxicity test is conducted under the following conditions.

(1) Apparatus
A: Apparatus accommodating Specimen No. 18 of this invention.
B: Apparatus accommodating Specimen No. 20 of this invention.
(2) Device
Chambers, 1 m×1 m×1 m (i.e. 1 m³).
(3) Animals
Five-week-old mice JCL: ICR
(4) Method
Five male mice or five female mice are placed into a chamber, the interior of the chamber is fumigated with one or two apparatus and the animals are left confined in the chamber for 2 hours. The animals are thereafter placed into an ordinary cage and given a diet and water.
(5) Results
Tables 9 and 10 show the results.

Table 9

| Test. No. | Apparatus | Number of deaths |  |  |  |  |  |
|---|---|---|---|---|---|---|---|
|  |  | Immediately after the fumigation |  | One day after the fumigation |  | Two days after the fumigation |  |
|  |  | M. | F. | M. | F. | M. | F. |
| 1 | A (one) | 0 | 0 | 0 | 0 | 0 | 0 |
| 2 | B (one) | 0 | 0 | 0 | 0 | 0 | 0 |
| 3 | B (two) | 0 | 0 | 0 | 0 | 0 | 0 |

Specimens No. 18 and No. 20 used in the toxicity test cause no death, and the test animals are alive 10 days after the fumigation. As shown in Table 9, high safety is ensured when using the present apparatus in a chamber having a concentration of the volatilized active ingredient over 30 times the concentration thereof at which a satisfactory insecticidal effect is achieved.

Table 10 shows the changes in the body weight of the animals surviving the test.

Table 10

| Test No. | Animal's sex | Body weight of the animals (average in g) |  |  |  |  |  |  |
|---|---|---|---|---|---|---|---|---|
|  |  | before test | 1 day after | 2 days after | 4 days after | 6 days after | 8 days after | 10 days after |
| 1 | M. | 26.2 | 27.3 | 26.2 | 29.6 | 29.4 | 29.6 | 31.4 |
|  | F. | 22.2 | 22.4 | 21.6 | 23.0 | 23.4 | 22.4 | 23.2 |
| 2 | M. | 24.8 | 26.2 | 25.6 | 28.4 | 27.0 | 28.4 | 29.8 |
|  | F. | 22.4 | 22.6 | 21.8 | 24.0 | 23.8 | 24.4 | 24.6 |
| 3 | M. | 25.4 | 28.4 | 28.2 | 31.0 | 31.4 | 31.8 | 34.0 |
|  | F. | 22.0 | 22.0 | 21.4 | 22.8 | 23.4 | 23.6 | 24.4 |

Table 10 reveals that the specimens of the invention show substantially no harmful effect on the increasing rate of body weight of the tested animals and that they are substantially free from toxicity. The amounts of food taken by the animals is slightly reduced only on the first day after the test but thereafter no change is observed.

Insecticidal Effect

1. Specimens of this invention are tested for insecticidal effect under the following conditions.

(1) Test insects
Adults of german cockroaches.

(2) Method
A laboratory dish (24 cm in inside diameter and 6.5 cm in height) containing 25 test insects is placed in each corner of a closed room, 3 m×4 m×3 m (height), i.e. 36 m³, and the interior of the room is fumigated with a specimen placed in the center of the room. Knockdown is determined at a specified time interval after the initiation of fumigation. Two hours after the fumigation, the test insects are transferred to a rearing chamber, and mortality (%) is determined in 24 hours and 48 hours. In the rearing chamber, the insects are given a diet and water. Table 11 shows the results.

Table 4

|  | Specimens No. | 11 | 24 | 25 | 20 |
|---|---|---|---|---|---|
|  | 30 min | 55 | 51 | 46 | 53 |
| Knockdown | 60 min. | 99 | 96 | 84 | 100 |
| (%) | 90 min. | 100 | 98 | 95 | 100 |
|  | 120 min. | 100 | 100 | 100 | 100 |
| Mortality | 24 hr. | 78 | 66 | 97 | 80 |
| (%) | 48 hr. | 100 | 100 | 100 | 100 |

Table 11 shows that the use of the present apparatus in a closed room leads to effective extermination of noxious vermin.

2. Specimen No. 20 of this invention is further tested for insecticidal effect in a simulated living room.

(1) Test insects
Adults of german cockroaches and adults of american cockroaches.

(2) Method
A 76-cm-high desk having four drawers in layers is placed in one corner of a room, 3 m in width, 4 m in length and 3 m in height, i.e. 36 m³. A wood box (45 cm×41 cm×37 cm) is placed in another corner of the room as spaced apart by 2 cm from the wall, with its opening opposed to the wall. A closed box (measureing 30 cm×30 cm×30 cm and having 8 holes of 7 mm in diameter in its top side) is placed on a 150-cm-high shelf in the center of one of the longitudinal walls of the room, the box being positioned close to the wall.

Laboratory dishes (24 cm in inside diameter and 6.5 cm in height) each containing 20 adults of german cockroaches and 10 adults of american cockroaches are placed in various locations within the room. The interior of the room is fumigated with a specimen placed in the center of the room, and the insects are left confined in the room for one hour. The insects are thereafter placed into a rearing case and given a diet and water. Mortality (%) is determined 24 hours and 48 hours after the start of the experiment.

The dishes are placed in the following locations:
$P_1$: In the open box.
$P_2$: In the closed box.
$P_3$: In the uppermost closed drawer of the desk.
$P_4$: In the second highest drawer of the desk as withdrawn by 1 cm.
$P_5$: In the lowermost drawer of the desk as withdrawn by 2 cm.

(3) Specimen
Specimen No. 20.

(4) Results
Table 12 shows the results achieved with the german cockroaches, and Table 13 those with american cockroaches.

Table 12

|  |  | Place | | | | |
|---|---|---|---|---|---|---|
|  |  | $P_1$ | $P_2$ | $P_3$ | $P_4$ | $P_5$ |
| Mortality | 24 hr. | 50 | 35 | 50 | 40 | 35 |
| (%) | 48 hr. | 100 | 95 | 100 | 100 | 100 |

Table 13

|  |  | Place | | | | |
|---|---|---|---|---|---|---|
|  |  | $P_1$ | $P_2$ | $P_3$ | $P_4$ | $P_5$ |
| Mortality | 24 hr. | 10 | 20 | 30 | 10 | 20 |
| (%) | 48 hr. | 90 | 60 | 100 | 80 | 100 |

Tables 12 and 13 show that the method of this invention is very effective at various locations.

EXAMPLE 5

The procedure of Example 1 is repeated using the same apparatus as used therein, the apparatus containing a fungicide and a blowing agent listed in Table 14, which also shows the results.

Table 14

| Specimen No. | Fungicide | (g) | Blowing agent | (g) | Effective fugacity rate (%) |
|---|---|---|---|---|---|
| 54 | IF-2 | 0.5 | AIBN | 5 | 60.1 |
| 55 | " | 0.5 | AC | 5 | 71.3 |
| 56 | " | 0.5 | AZ-A | 10 | 66.7 |
| 57 | IF-8 | 0.5 | AZ-B | 10 | 66.8 |
| 58 | " | 0.5 | AIBN | 5 | 68.4 |
| 59 | " | 0.5 | ACHC | 5 | 57.8 |
| 60 | IF-7 | 0.5 | AZ-B | 5 | 57.9 |
| 61 | " | 0.5 | AC | 5 | 70.8 |
| 62 | " | 0.5 | CIB | 5 | 54.0 |
| 63 | IF-6 | 0.5 | DPT | 1.5 | 68.4 |
| 64 | IF-3 | 0.5 | AZ-A | 3 | 88.8 |
| 65 | IF-2 | 0.5 | AIBN | 10 | 71.3 |
| 66 | IF-1 | 0.5 | AIBN | 5 | 71.5 |
| 67 | IF-4 | 0.5 | AIBN | 5 | 54.0 |
| 68 | IF-3 | 1 | AZ-A | 2 | 56.4 |
|  |  |  | AZ-B | 2 |  |

COMPARATIVE EXAMPLE 4

The procedure of Example 5 is repeated using an fungicide listed in Table 15 but without using any blowing agent. Table 15 also shows the results.

Table 15

| Specimen No. | Fungicide | (g) | Effective fugacity rate (%) |
|---|---|---|---|
| 69 | IF-5 | 1 | 6.5 |
| 70 | IF-8 | 1 | 8.9 |
| 71 | IF-7 | 1 | 18 |
| 72 | IF-2 | 1 | 10.8 |

Tables 14 and 15 reveal that the use of a blowing agent conjointly with a fungicide enables the fungicide to volatilize with an efficiency which is 10-odd times as high as the efficiency achieved by the same quantity of the fungicide at the same temperature.

What we claim is:

1. A fumigating apparatus comprising a container having at least one compartment accommodating a mixture of an active ingredient and a blowing agent which is decomposable at a temperature of between about 70° C. and about 300° C. to give off mainly nitrogen gas and at least one further compartment provided adjacent to said compartment and accommodating an exothermic substance which evolves heat by contact with water, the interior of the container being divided with a partition into said compartments, the partition providing a surface for transferring the heat evolved from said exothermic substance to the mixture, the compartment accommodating the exothermic substance being provided with water supplying means.

2. An apparatus as defined in claim 1 wherein the exothermic substance is calcium oxide.

3. An apparatus as defined in claim 1 wherein the active ingredient is an insecticide.

4. An apparatus as defined in claim 1 wherein the active ingredient is a fungicide.

5. An apparatus as defined in claim 1 wherein the partition is horizontal, and the mixture is positioned above and separated from the exothermic substance with the horizontal partition interposed therebetween.

6. An apparatus as defined in claim 1 wherein the mixture accommodating compartment has an open upper end sealed with a meltable film.

7. An apparatus as defined in claim 1 wherein a water-permeable layer is provided within the closed compartment to permit the water supplied from the water supplying means to pass through the layer into contact with the exothermic substance.

8. An apparatus as defined in claim 1 wherein the container is provided with means for attaching the apparatus to a vertical wall, column surface or ceiling.

9. An apparatus as defined in claim 1 wherein the container is provided with means for supplying a specified amount of water to the compartment accommodating the exothermic substance.

10. An apparatus as defined in claim 1 wherein the partition is vertical to separate the mixture and the exothermic substance from each other.

11. An apparatus as defined in claim 10 wherein the mixture and the exothermic substance are arranged concentrically with each other when seen in plan.

12. An apparatus as defined in claim 1 wherein said blowing agent is at least one species selected from the group consisting of azodicabonamide, benzensulfonylhydrazide, p-toluenesulfonylhydrazide, p,p'-oxybis(-benzenesulfonylhydrazide), dinitrosopentamethylenetetramine, N,N'-dinitroso-N,N'-dimethylterephthalamide, trihydrazinotriazine, azobisisobutyronitrile, 4,4'-azobiscyanovaleric acid, t-butylazoformamide, 2,4-bis(azosulfonyl)toluene, 2,2'-azobisisobutyloamide, methyl-2,2'-azobisisobutyrate, 2-(carbamoylazo)isobutyronitrile and 1,1'-azobiscyclohexane-1-carbonitrile.

13. An apparatus as defined in claim 12 wherein the blowing agent is azodicarbonamide.

14. An apparatus as defined in claim 1 wherein the mixture and the exothermic substance are horizontally and vertically separated from each other by the partition, the mixture being positioned on and beside the partition, the exothermic substance being positioned beneath and beside the partition.

15. An apparatus as defined in claim 14 wherein the mixture and the exothermic substance are arranged concentrically with each other when seen in plan.

16. An apparatus as defined in claim 15 wherein the mixture accommodating compartment is divided into at least two.

17. An apparatus as defined in claim 1 wherein the compartment accommodating the exothermic substance is substantially closed.

18. An apparatus as defined in claim 17 wherein the water supplying means is at least one water inlet aperture formed in an upper portion of the closed compartment.

19. An apparatus as defined in claim 17 wherein the water supplying means is at least one water inlet aperture formed in a lower portion of the exothermic substance accommodating compartment.

20. An apparatus as defined in claim 17 wherein the closed compartment is provided with a water receptacle in its top portion, and the water inlet aperture is formed in the bottom of the water receptacle.

21. An apparatus as defined in claim 17 wherein the water supplying means is a water reservoir provided within the closed compartment, and the water reservoir is provided with means for opening the reservoir from outside.

22. An apparatus as defined in claim 17 wherein the closed compartment is provided with an opening for maintaining the internal pressure of the closed compartment in balance with the outside pressure.

23. A fumigating method comprising heating indirectly a mixture of an active ingredient and a blowing agent with heat evolved from an exothermic substance which evolves heat by contact with water, thereby decomposing the blowing agent and volatilizing the active ingredient, said blowing agent being decomposable at a temperature of between about 70° C. and about 300° C. to give off mainly nitrogen gas and contacting an object, material or area to be treated with the so generated fumigant.

24. A fumigating method as defined in claim 23 wherein the active ingredient is an insecticide.

25. A fumigating method as defined in claim 23 wherein the active ingredient is a fungicide.

26. A fumigating method as defined in claim 23 wherein the exothermic substance is calcium oxide.

27. A fumigating method as defined in claim 23 wherein said blowing agent is at least one species selected from the group consisting of azodicarbonamide, benzenesulfonylhydrazide, p-toluenesulfonylhydrazide, p,p'-oxybis(benzenesulfonylhydrazide), dinitrosopentamethylenetetramine, N,N'-dinitroso-N,N'-dimethylterephthalamide, trihydrazinotriazine, azobisisobutyronitrile, 4,4'-azobiscyanovaleric acid, t-butylazoformamide, 2,4-bis(azosulfonyl)toluene, 2,2'-azobisisobutyloamide, methyl-2,2'-azobisisobutyrate, 2-(carbamoylazo)isobutyronitrile and 1,1'-azobiscyclohexane-1-carbonitrile.

28. A fumigating method as defined in claim 27 wherein said blowing agent is at least one species selected from the group consisting of azodicarbonamide, p,p'-oxybis(benzenesulfonylhydrazide), dinitrosopentamethylenetetramine, azobisisobutyronitrile and 1,1'-azobiscyclohexane-1-carbonitrile.

29. A fumigating method as defined in claim 2 wherein the blowing agent is azodicarbonamide.

* * * * *

REEXAMINATION CERTIFICATE (482nd)

United States Patent [19]
Nishimura et al.

[11] B1 4,171,340
[45] Certificate Issued Apr. 8, 1986

[54] FUMIGATING APPARATUS AND METHOD

[75] Inventors: Akira Nishimura; Takanobu Kashihara; Fukuyasu Okuda; Masanaga Yamaguchi, all of Ako, Japan

[73] Assignee: Earth Chemical Company, Ltd., Hyogo, Japan

Reexamination Request:
No. 90/000,630, Sep. 17, 1984

Reexamination Certificate for:
Patent No.: 4,171,340
Issued: Oct. 16, 1979
Appl. No.: 882,816
Filed: Mar. 2, 1978

[30] Foreign Application Priority Data

| Mar. 3, 1977 | [JP] | Japan | 52-23475[U] |
| Mar. 18, 1977 | [JP] | Japan | 52-33445[U] |
| Mar. 18, 1977 | [JP] | Japan | 52-33446[U] |
| Apr. 27, 1977 | [JP] | Japan | 52-54648[U] |
| May 13, 1977 | [JP] | Japan | 52-61975[U] |
| Jun. 6, 1977 | [JP] | Japan | 52-74167[U] |
| Jul. 23, 1977 | [JP] | Japan | 52-98584[U] |

[51] Int. Cl.[4] .................. A61L 2/22; A61L 9/03; A01M 13/00
[52] U.S. Cl. .................. 422/36; 43/125; 43/129; 71/DIG. 1; 252/350; 422/1; 422/28; 422/37; 422/305; 424/40
[58] Field of Search ........... 422/28-37, 422/39, 125, 305, 120, 125, 126; 424/40; 252/50

[56] References Cited

U.S. PATENT DOCUMENTS

| 586,759 | 7/1897 | Cock | 422/305 |
| 1,652,291 | 12/1927 | Tanner | 424/297 |
| 2,497,612 | 2/1950 | Katzman | 422/125 |
| 2,540,095 | 2/1951 | Buehler | 422/305 X |
| 2,690,501 | 9/1954 | Laibow | 422/28 X |
| 2,767,511 | 10/1956 | Kissner et al. | 422/305 X |
| 3,042,580 | 7/1962 | Jacobi | 424/40 |
| 3,645,931 | 2/1972 | Normanton | 252/350 X |
| 3,806,323 | 4/1974 | Thompson | 422/126 X |
| 3,903,015 | 9/1975 | Roos et al. | 252/350 |
| 3,986,838 | 10/1976 | Reichert | 422/126 |

FOREIGN PATENT DOCUMENTS

| 428800 | 4/1967 | Japan . |
| 452390 | 8/1970 | Japan . |
| 699766 | 11/1953 | United Kingdom . |

*Primary Examiner*—Barry S. Richman
*Assistant Examiner*—Brion P. Heaney

[57] ABSTRACT

A mixture of an active ingredient such as insecticide, fungicide, antiseptic or the like and a blowing agent is heated indirectly with a heat evolved by contacting an exothermic substance with water to decompose the blowing agent and to volatilize the active agent *without combustion*. The mixture is accommodated in at least one compartment of a container while the exothermic substance is accommodated in at least one further compartment provided with water supplying means, said compartments being separated from each other by a partition which provides a heat transferring surface.

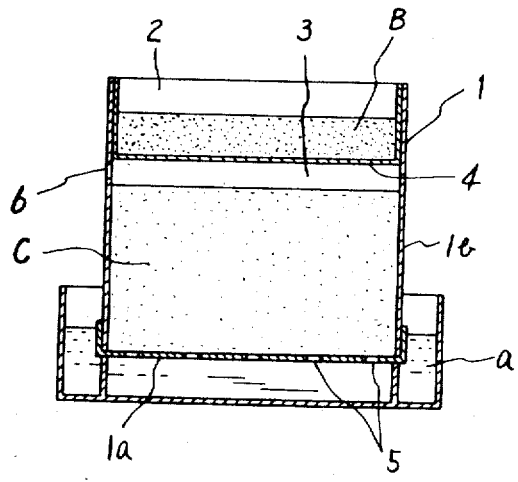

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2 and 26 are cancelled.

Claims 1, 7, 12, 20, 23, 27 and 29 are determined to be patentable as amended.

Claims 3–6, 8–11, 13–19, 21, 22, 24, 25, and 28 dependent on an amended claim, are determined to be patentable.

New claims 30 and 31 are added and determined to be patentable.

1. A fumigating apparatus comprising a container having at least one compartment accommodating a mixture of an active ingredient and a blowing agent [which is], *said blowing agent being selected from those* decomposable at a temperature of between about 70° C. and about 300° C. *without combustion* to give off mainly nitrogen gas, and at least one further compartment provided adjacent to said compartment and accommodating an exothermic substance which evolves heat by contact with water, *said exothermic substance being calcium oxide*, the interior of the container being divided with a partition into said compartments, the partition providing a surface for transferring the heat evolved from said exothermic substance to the mixture, the compartment accommodating the exothermic substance being provided with water supplying means *with the proviso that the relative amounts of exothermic substance and the mixture are such that the exothermic substance is in capable of generating sufficient heat from its reaction with water for transfer to the mixture to exceed the combustion temperature of said mixture.*

7. An apparatus as defined in claim 1 wherein *the compartment accommodating the exothermic substance is substantially closed and* a water-permeable layer is provided within the closed compartment to permit the water supplied from the water supplying means to pass through the layer into contact with the exothermic substance.

12. An apparatus as defined in claim 1 wherein said blowing agent is at least one species selected from the group consisting of azodicabonamide, benzensulfonylhydrazide, p-toluenesulfonylhydrazide, p,p'-oxybis(benzenesulfonylhydrazide), dinitrosopentamethylenetetramine, N,N'-dinitroso-N,N'-dimethylterephthalamide, trihydrazinotriazine, azobisisobutyronitrile, 4,4'-azobiscyanovaleric acid, t-butylazoformamide, 2,4-bis(azosulfonyl)toluene, [2,2'-azobisisobutyloamide] *2,2'-azobisisobutyroamide*, methyl-2,2'-azobisisobutyrate, 2-(carbamoylazo)isobutyronitrile and 1,1'-azobiscyclohexane-1-carbonitrile.

20. An apparatus as defined in claim 17 wherein the closed compartment is provided with a water receptacle in its top portion, and [the] *said water supplying means comprises a* water inlet aperture [is] formed in the bottom of the water receptacle, *said inlet aperature being in fluid communication with said closed compartment.*

23. A rumigating method comprising heating indirectly a mixture of an active ingredient and a blowing agent with heat evolved from an exothermic substance which evolves heat by contact with water, *said blowing agent being selected from those decomposable at a temperature of between about 70° C. and about 300° C. without combustion to give off mainly nitrogen gas*, said exothermic substance being calcium oxide, thereby decomposing the blowing agent *without combustion* and volatizing the active ingredient, [said blowing agent being decomposable at a temperature of between about 70° C. and about 300° C. to give off mainly nitrogen gas] and contacting an object, material or area to be treated with the [so generated fumigant] *volatized active ingredient.*

27. A rumigating method as defined in claim 23 wherein said blowing agent is at least one species selected from the group consisting of azodicarbonamide, benzensulfonylhydrazide, p-toluenesulfonylhydrazide, p,p'-oxybis(benzenesulfonylhydrazide), dinitrosopentamethylenetetramine, N,N'-dinitroso-N,N'-dimethylterephthalamide, trihydrazinotriazine, azobisisobutyronitrile, 4,4'-azobiscyanovaleric acid, t-butylazoformamide, [2,4-bis(azosulfonyl)toluene, 2,2'-azobisisobutyloamide] *2,4-bis-(azosulfonyl)toluene, 2,2'-azobisisobutyroamide*, methyl-2,2'-azobisisobutyrate, 2-(carbamoylazo)isobutyronitrile and 1,1'-azobiscyclohexane-1-carbonitrile.

29. A fumigating method as defined in claim [2] *28* wherein the blowing agent is azodicarbonamide.

*30. A fumigating apparatus comprising a container having at least one compartment accommodating a mixture of an active ingredient and a blowing agent, said blowing agent being decomposable at a temperature of between 70° C. and 300° C. without combustion to give off mainly nitrogen gas, said blowing agent being selected from the group consisting of azodicarbonamide, p,p'-oxybis(benzenesulfonylhydrazide), trihydrazinotriazine, azobisisobutyronitrile, 4,4'-azobiscyanovaleric acid, t-butylazoformamide, 2,4-bis-(azosulfonyl)toluene, 2,2'-azobisisobutyramide, methyl-2,2'-azobisisobutyrate, 2-(carbamoylazo)isobutyronitrile, and 1,1'-azobiscyclohexane-1-carbonitrile, and at least one further compartment provided adjacent to said compartment and accommodating an exothermic substance which evolves heat by contact with water, said exothermic substance being calcium oxide, the interior of the container being divided with a partition into said compartments, the partition providing a surface for transferring the heat evolved from said exothermic substance to the mixture, the compartment accommodating the exothermic substance being provided with water supplying means with the proviso that the relative amounts of the exothermic substance and the mixture are such that the exothermic substance is incapable of generating sufficient heat from its reaction with water for transfer to the mixture to exceed the combustion temperature of said mixture.*

*31. A fumigating method comprising heating indirectly a mixture of an active ingredient and a blowing agent with*

*heat evolved from an exothermic substance which evolves heat by contact with water, said blowing agent being decomposable at a temperature of between 70° C. and 300° C. without combustion to give off mainly nitrogen gas, said blowing agent being selected from the group consisting of azodicarbonamide, p,p'-oxybis(benzenesulfonylhydrazide), trihydrazinotriazine, azobisisobutyronitrile, 4,4'-azobiscyanovaleric acid, t-butylazoformamide, 2,4-bis-(azobiscyanovaleric acid, t-butylazoformamide, 2,4-bis-(azosulfonyl)toluene, 2,2'-azobisisobutyroamide, methyl-2,2'-azobisisobutyrate, 2-(carbamoylazo)isobutyronile, and 1,1'-azobiscyclohexane-1-carbonitrile, said exothermic substance being calcium oxide, thereby decomposing the blowing agent without combustion and volatilizing the active ingredient, and contacting an object, material or area to be treated with the volatized active ingredient.*

* * * * *